United States Patent
Whitfield et al.

(10) Patent No.: US 11,350,915 B2
(45) Date of Patent: Jun. 7, 2022

(54) SURGICAL STAPLER WITH SMALL DIAMETER ENDOSCOPIC PORTION

(71) Applicant: Covidien LP, Mansfield, MA (US)

(72) Inventors: Kenneth Whitfield, North Haven, CT (US); Thomas Casasanta, Jr., Southington, CT (US); Timothy Ebner, Southington, CT (US); Anthony Gaddy, Windsor, CT (US)

(73) Assignee: Covidien LP, Mansfield, MA (US)

( * ) Notice: Subject to any disclaimer, the term of this patent is extended or adjusted under 35 U.S.C. 154(b) by 250 days.

(21) Appl. No.: 16/297,055

(22) Filed: Mar. 8, 2019

(65) Prior Publication Data

US 2019/0200971 A1 Jul. 4, 2019

Related U.S. Application Data

(63) Continuation-in-part of application No. 15/440,010, filed on Feb. 23, 2017, now Pat. No. 10,849,621.

(51) Int. Cl.
*A61B 17/00* (2006.01)
*A61B 17/072* (2006.01)
(Continued)

(52) U.S. Cl.
CPC ...... *A61B 17/00234* (2013.01); *A61B 17/072* (2013.01); *A61B 17/07207* (2013.01);
(Continued)

(58) Field of Classification Search
CPC ............ A61B 17/00234; A61B 17/047; A61B 17/07207; A61B 2017/0046;
(Continued)

(56) References Cited

U.S. PATENT DOCUMENTS

| | | |
|---|---|---|
| 3,499,591 A | 3/1970 | Green |
| 3,777,538 A | 12/1973 | Weatherly et al. |

(Continued)

FOREIGN PATENT DOCUMENTS

| | | |
|---|---|---|
| AU | 198654765 | 9/1986 |
| CA | 2773414 A1 | 11/2012 |

(Continued)

OTHER PUBLICATIONS

Partial European Search Report dated Jul. 23, 2018 in EP Appln. No. 18158201.

(Continued)

*Primary Examiner* — Chelsea E Stinson
*Assistant Examiner* — Scott A Howell
(74) *Attorney, Agent, or Firm* — Carter, DeLuca & Farrell LLP

(57) ABSTRACT

A surgical stapler including a shipping lock configured to obstruct movement of a drive member is provided. The surgical stapler includes an elongate body, a tool assembly pivotally secured to the elongate body, a drive member movable within the tool assembly between retracted and advanced positions, and a shipping lock releasably secured to the elongate body. The shipping lock includes a projection. When the shipping lock is secured to the elongate body, the projection obstructs movement of the drive member to its advanced position.

13 Claims, 27 Drawing Sheets

(51) Int. Cl.
*A61B 90/00* (2016.01)
*A61B 17/29* (2006.01)

(52) U.S. Cl.
CPC ...... *A61B 90/03* (2016.02); *A61B 2017/0046* (2013.01); *A61B 2017/00464* (2013.01); *A61B 2017/00473* (2013.01); *A61B 2017/07221* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2090/038* (2016.02)

(58) Field of Classification Search
CPC   A61B 2017/00464; A61B 2017/00473; A61B 2017/07221; A61B 2017/07257; A61B 2017/07271; A61B 2017/07287; A61B 2017/2927; A61B 2090/038
See application file for complete search history.

(56) References Cited

U.S. PATENT DOCUMENTS

| | | |
|---|---|---|
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Mien et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Ley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Ley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |

(56) References Cited

U.S. PATENT DOCUMENTS

| | | |
|---|---|---|
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |

(56) References Cited

U.S. PATENT DOCUMENTS

| | | |
|---|---|---|
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |

(56) References Cited

U.S. PATENT DOCUMENTS

| | | | |
|---|---|---|---|
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 * | 8/2010 | Scirica ............ A61B 17/07207 227/175.2 |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |

(56) References Cited

U.S. PATENT DOCUMENTS

| | | |
|---|---|---|
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,066,167 B2 | 11/2011 | Measamer et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 * | 7/2012 | Farascioni ....... A61B 17/07207 227/175.2 |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |

(56) References Cited

U.S. PATENT DOCUMENTS

| | | |
|---|---|---|
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,556 B2 * | 12/2012 | Zergiebel ............... A61B 34/76 128/898 |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 * | 3/2013 | Kostrzewski ........ A61B 17/068 227/175.2 |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 * | 4/2013 | Farascioni ....... A61B 17/07207 227/175.2 |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |

(56) References Cited

U.S. PATENT DOCUMENTS

| | | |
|---|---|---|
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,701,962 B2 * | 4/2014 | Kostrzewski ...... A61B 17/0686 227/175.2 |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,807,414 B2 | 8/2014 | Ross et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |

(56) References Cited

U.S. PATENT DOCUMENTS

| | | |
|---|---|---|
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,662 B2 | 8/2015 | Kostrzewski |
| 9,107,663 B2 | 8/2015 | Swensgard |
| 9,107,664 B2 | 8/2015 | Marczyk |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,661 B2 | 12/2015 | Swensgard |
| 9,204,876 B2 | 12/2015 | Cappola et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,474,578 B2 | 10/2016 | Farascioni et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 * | 12/2016 | Kostrzewski ........ A61B 17/068 |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 9,706,993 B2 | 7/2017 | Hessler et al. |
| 9,707,005 B2 | 7/2017 | Strobl et al. |
| 9,757,126 B2 | 9/2017 | Cappola |
| 9,775,611 B2 * | 10/2017 | Kostrzewski .... A61B 17/07207 |
| 9,820,737 B2 | 11/2017 | Beardsley et al. |
| 9,855,040 B2 * | 1/2018 | Kostrzewski .... A61B 17/07207 |
| 10,045,781 B2 | 8/2018 | Cropper et al. |
| 10,045,782 B2 | 8/2018 | Murthy Aravalli |
| 10,085,748 B2 | 10/2018 | Morgan et al. |
| 10,085,750 B2 | 10/2018 | Zergiebel et al. |
| 10,117,649 B2 | 11/2018 | Baxter, III et al. |
| 10,188,385 B2 | 1/2019 | Kerr et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0184124 A1 | 8/2005 | Scirica et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0226195 A1 | 10/2006 | Scirica et al. |
| 2006/0289602 A1 | 12/2006 | Wales et al. |
| 2007/0029364 A1 | 2/2007 | Kruszynski et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0114700 A1 | 5/2009 | Marczyk |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |

(56) References Cited

U.S. PATENT DOCUMENTS

| | | |
|---|---|---|
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163148 A1 | 7/2011 | Wenchell et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0223121 A1 | 9/2012 | Viola et al. |
| 2012/0234894 A1* | 9/2012 | Kostrzewski .... A61B 17/07207 227/175.2 |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0284372 A1* | 9/2014 | Kostrzewski .... A61B 17/07207 227/177.1 |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |

(56) References Cited

U.S. PATENT DOCUMENTS

| | | |
|---|---|---|
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0209040 A1 | 7/2015 | Whitman et al. |
| 2015/0250474 A1 | 9/2015 | Abbott et al. |
| 2015/0297225 A1 | 10/2015 | Huitema et al. |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0106418 A1 * | 4/2016 | Shi ............... A61B 17/068 227/175.2 |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |
| 2017/0231633 A1 | 8/2017 | Marczyk et al. |
| 2017/0290584 A1 * | 10/2017 | Jasemian ......... A61B 17/07207 |
| 2019/0200971 A1 * | 7/2019 | Whitfield ......... A61B 17/00234 |

FOREIGN PATENT DOCUMENTS

| | | |
|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1709911 | 10/2006 |
| EP | 1908414 A2 | 4/2008 |
| EP | 1952769 A2 | 8/2008 |
| EP | 2090253 A2 | 8/2009 |
| EP | 2090254 A1 | 8/2009 |

(56) References Cited

FOREIGN PATENT DOCUMENTS

| | | |
|---|---|---|
| EP | 2316349 A1 | 5/2011 |
| EP | 2499987 A2 | 9/2012 |
| EP | 2583630 A2 | 4/2013 |
| EP | 2586382 A2 | 5/2013 |
| EP | 2907456 A1 | 8/2015 |
| EP | 3064143 A1 | 9/2016 |
| EP | 3120780 A2 | 1/2017 |
| EP | 3205291 A1 | 8/2017 |
| EP | 3338683 | 6/2018 |
| EP | 3375386 A2 | 9/2018 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2011092707 A | 5/2011 |
| JP | 2014176664 A | 9/2014 |
| JP | 2014184142 A | 10/2014 |
| JP | 2015196085 A | 11/2015 |
| JP | 2017023720 A | 2/2017 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004/032760 A2 | 4/2004 |
| WO | 2004096057 A2 | 11/2004 |
| WO | 2009071070 A2 | 6/2009 |
| WO | 20150191887 A1 | 12/2015 |

OTHER PUBLICATIONS

European Search Report dated Nov. 6, 2018, issued in European Appln. No. EP18158201.
European Search Report dated May 20, 2020, issued in EP Appln. No. 20161545, 9 pages.
European Communication dated Jul. 8, 2021, corresponding to counterpart European Application No. 18158201.6; 7 pages.
European Search Report dated Feb. 14, 2022, corresponding to counterpart European Application No. 21208308.3; 8 pages.
English translation of Chinese Office Action dated Dec. 21, 2021, corresponding to counterpart Chinese Application No. 2018-026890; 5 pages.

\* cited by examiner

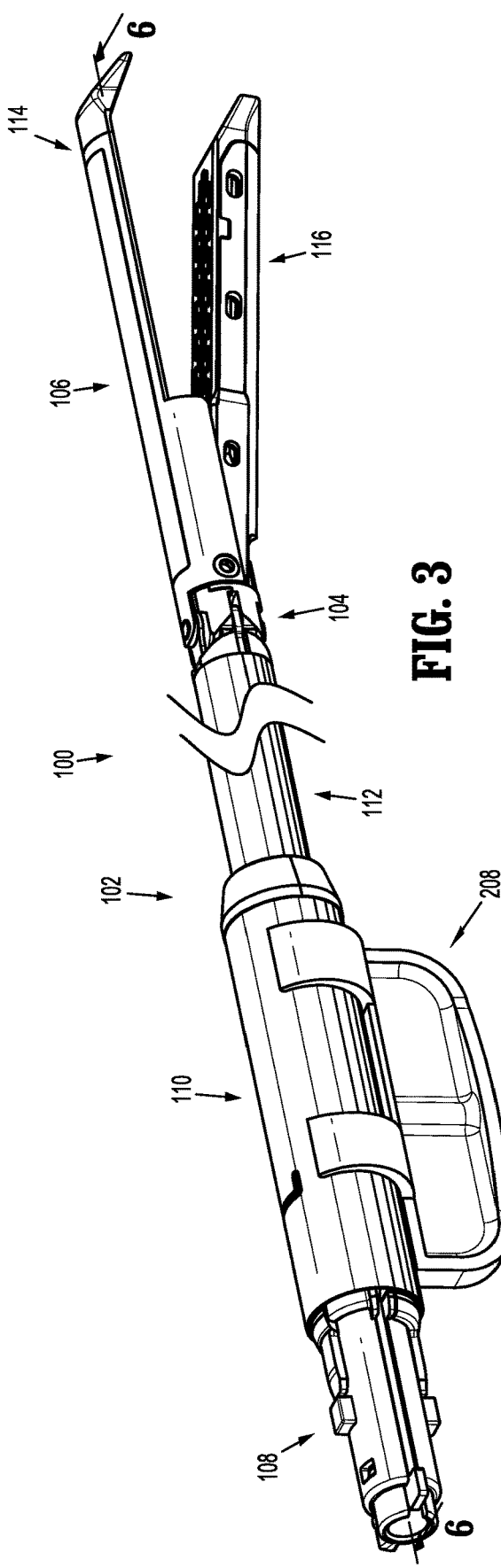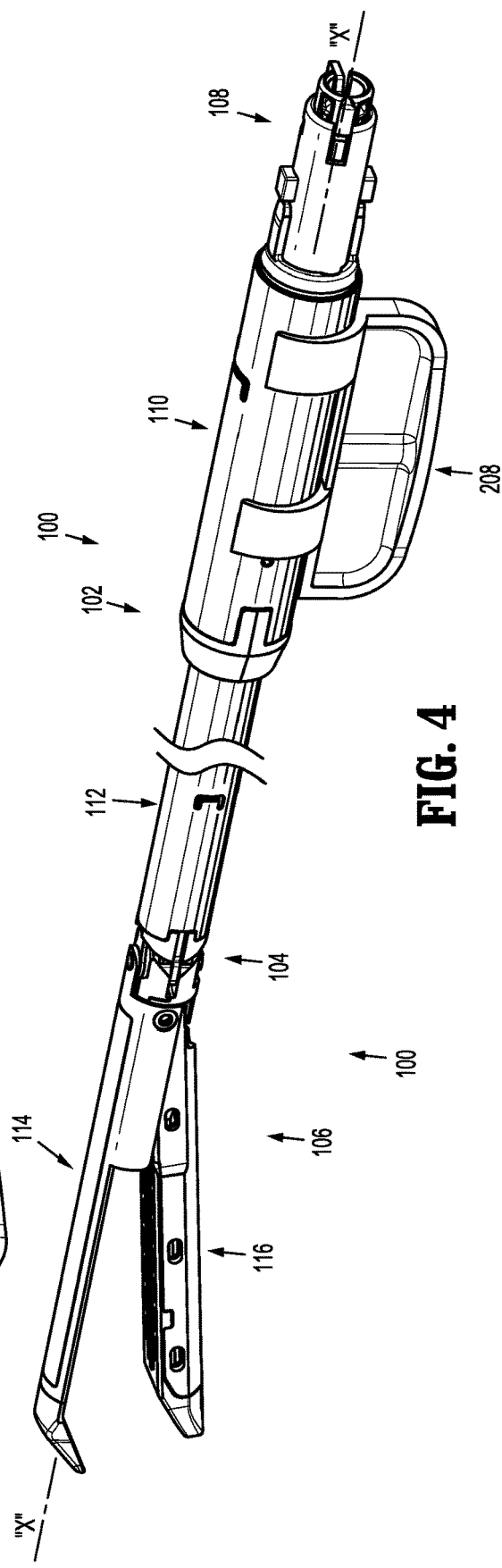

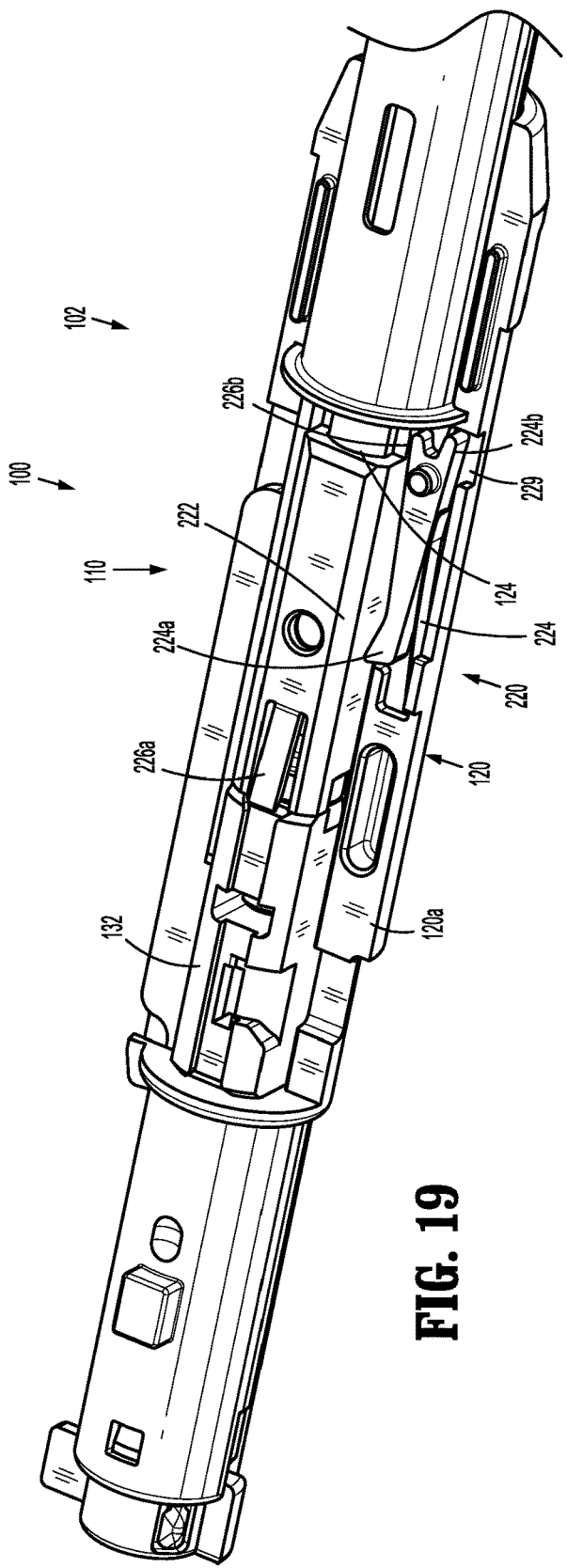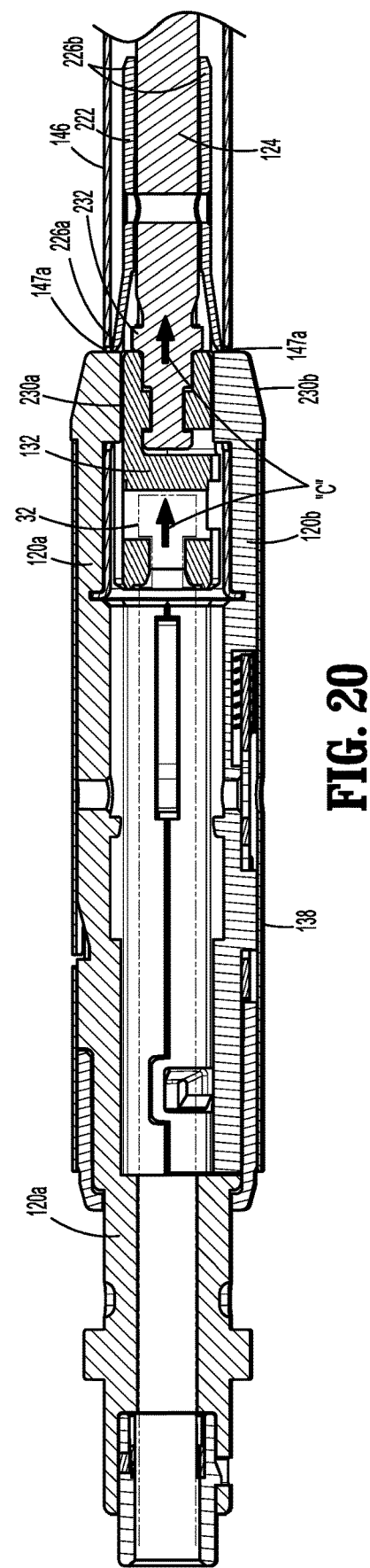
FIG. 19
FIG. 20

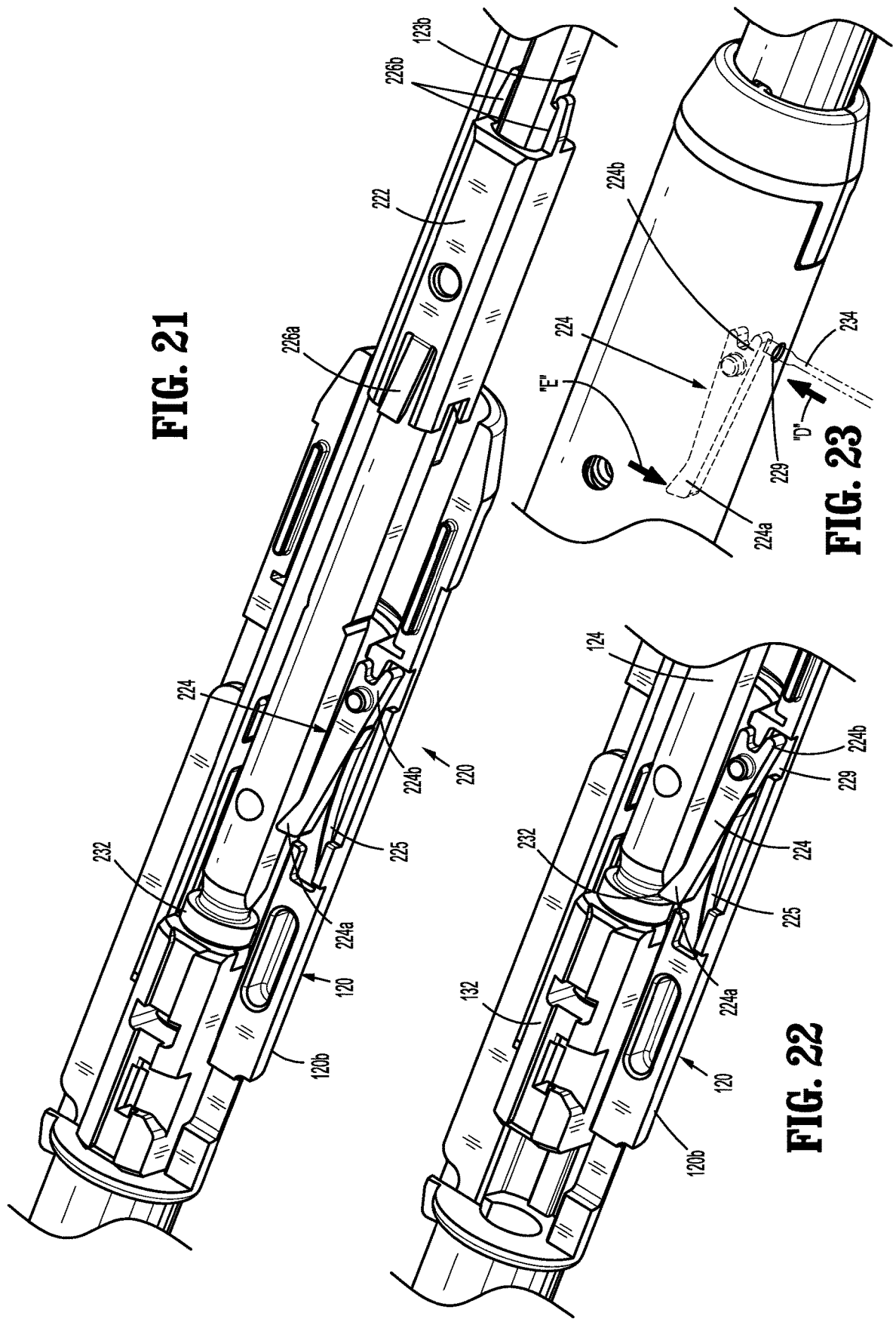

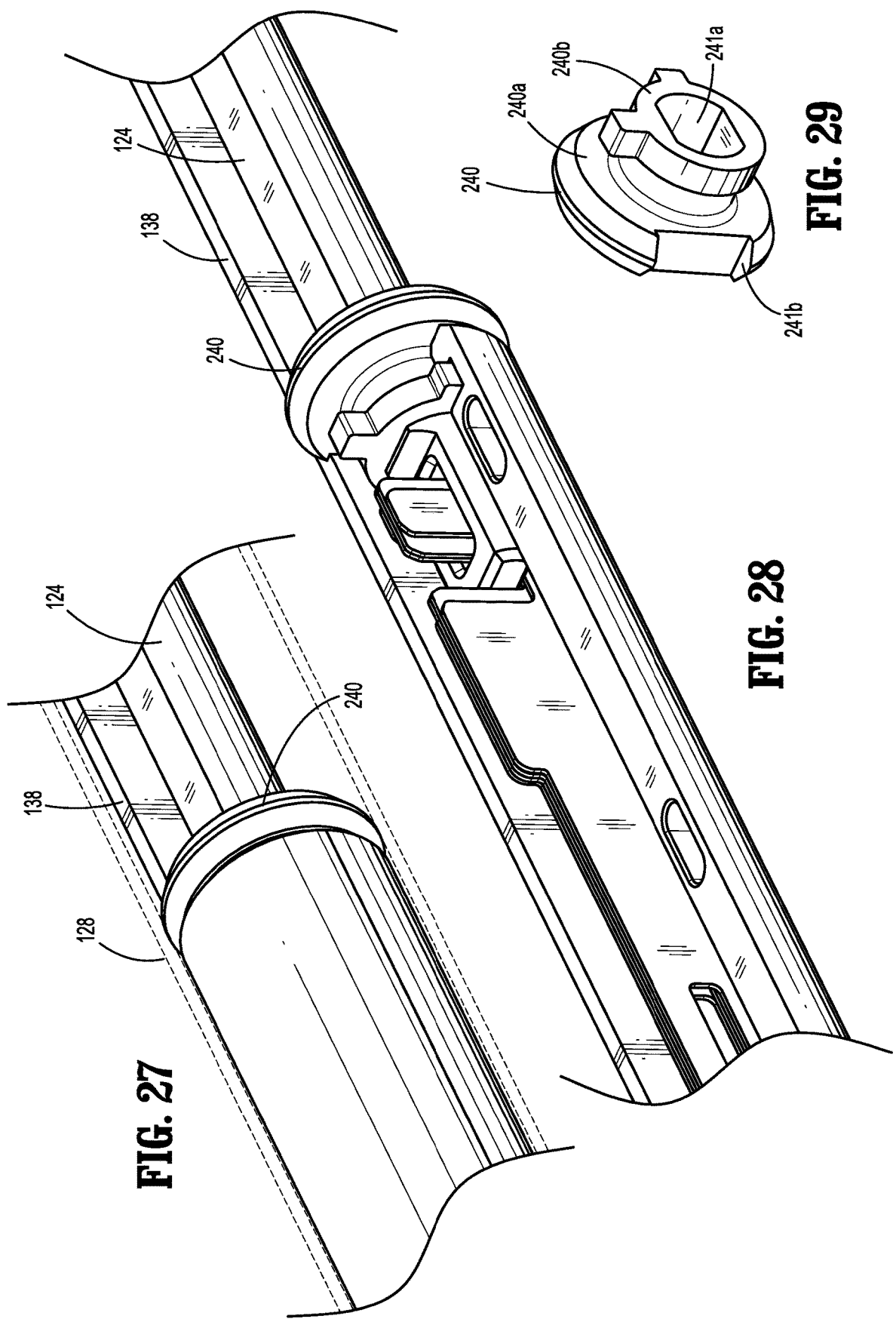

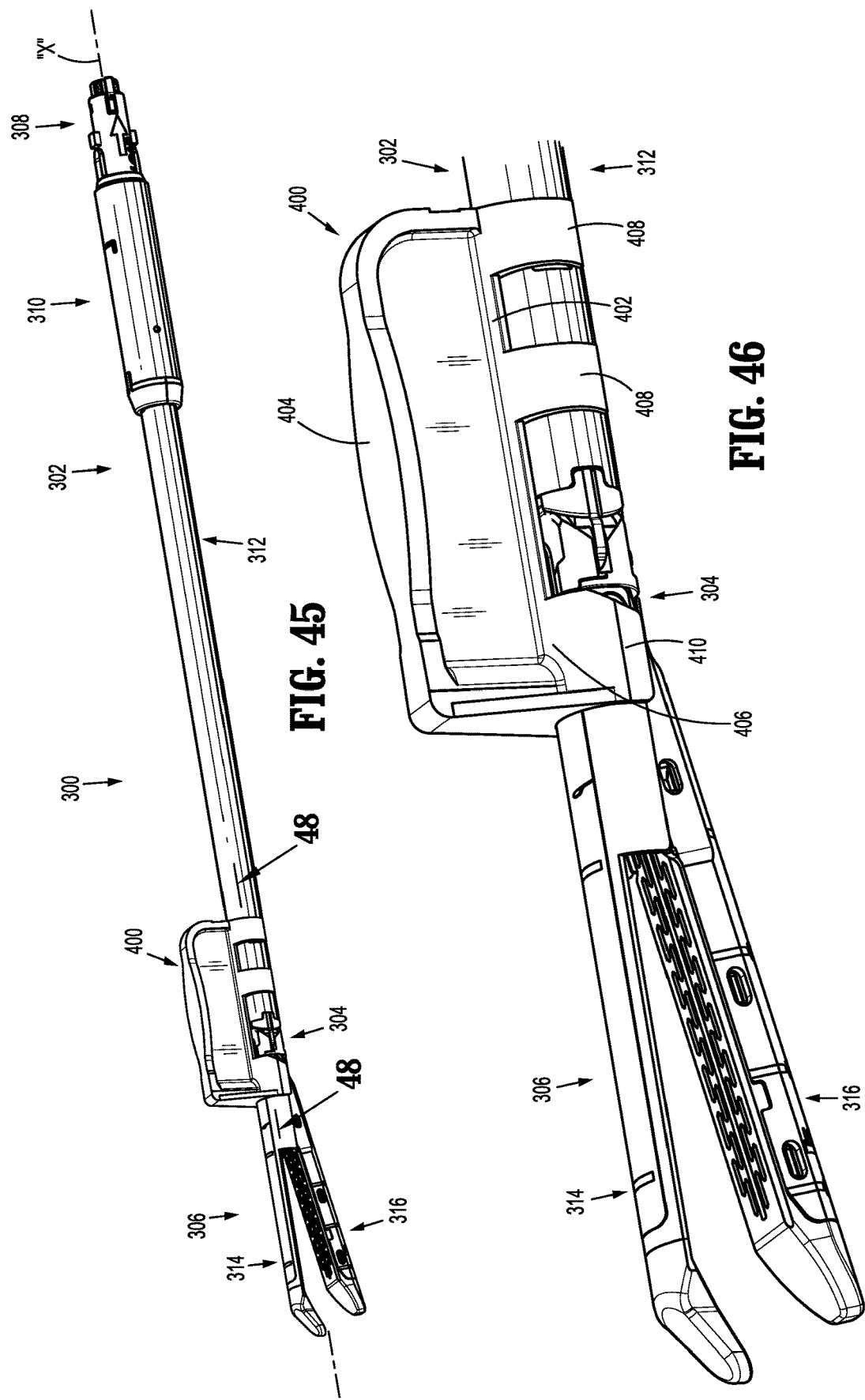

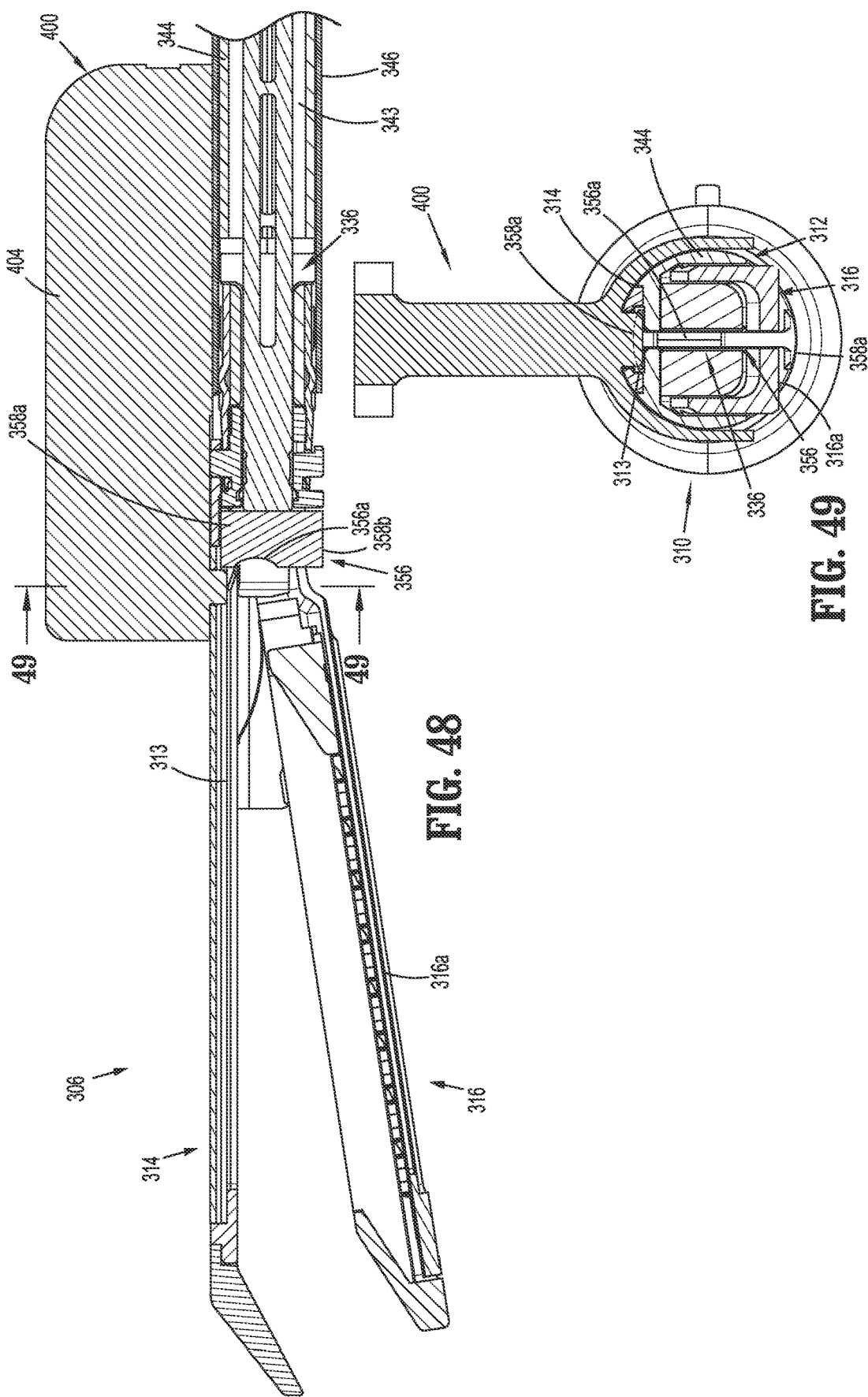

SURGICAL STAPLER WITH SMALL DIAMETER ENDOSCOPIC PORTION

CROSS-REFERENCE TO RELATED APPLICATIONS

The present application is a continuation-in-part of U.S. patent application Ser. No. 15/440,010, filed on Feb. 23, 2017, the content of which is incorporated by reference herein in its entirety.

BACKGROUND

Technical Field

The present disclosure relates to surgical staplers, and, more particularly, to endoscopic surgical staplers including small diameter endoscopic portions suitable for performing endoscopic surgical procedures including, inter alia, pediatric and thoracic surgical procedures.

Background of Related Art

Surgical staplers that effect simultaneous dissection and suturing of tissue are well known in the art. The advent of surgical staplers has increased the speed of tissue suturing and thus, increased the speed of surgical procedures to reduce patient trauma.

Endoscopic surgical staplers for suturing tissue endoscopically through small incisions in the skin or through a cannula rather than by performing open surgical procedures are also well known in the art and have also reduced patient trauma.

Typically endoscopic surgical staplers include an elongated body that supports a tool assembly. The elongated body and tool assembly (endoscopic portion) are dimensioned to pass through the small incision in the skin or the cannula. It is advantageous to minimize the dimensions of the elongated body and the tool assembly to minimize trauma to the patient. Thus, a continuing need exists for small diameter surgical staplers suitable for endoscopic use.

SUMMARY

In accordance with the present disclosure, a surgical stapler is provided that includes a body portion that has a distal portion of a reduced diameter to facilitate insertion of the endoscopic portion through a small diameter trocar assembly. The surgical stapler includes an actuation device, and a stapler reload releasably secured to the actuation device. The stapler reload includes a body portion, a tool assembly, and a drive assembly movable within tool assembly. The body portion includes a large diameter portion defining a first diameter and a small diameter portion defining a second diameter extending distally from the large diameter portion. The tool assembly is supported on a distal portion of the small diameter portion. The small diameter portion is dimensioned to pass through an 8 mm trocar. The surgical stapler further includes a shipping lock releasably secured to the distal portion of the small diameter portion of the body portion. The shipping lock is engageable with the drive assembly for preventing longitudinal movement of the drive assembly.

In embodiments, the shipping lock is configured to prevent articulation of the tool assembly relative to the body portion. The shipping lock may include a locking portion that engages the tool assembly to prevent articulation of the tool assembly relative to the body portion. The tool assembly may include an anvil assembly and a cartridge assembly supporting a plurality of staples. The drive assembly may be movable through the tool assembly to eject the plurality of staples from the cartridge assembly.

The drive assembly may include a clamping member and the shipping lock may include a projection. The projection may engage the clamping member when the shipping lock is secured to the body portion to obstruct advancement of the drive assembly. The clamping member may include an upper flange. The projection of the shipping lock may engage the upper flange to prevent advancement of the drive assembly. The shipping lock may include curved arms configured to frictionally engage the body portion of the stapler reload.

Also provided is a surgical stapler with a shipping lock configured to obstruct movement of a drive member. The surgical stapler includes an elongate body, a tool assembly pivotally secured to the elongate body, a drive member movable within the tool assembly between retracted and advanced positions, and a shipping lock releasably secured to the elongate body. The shipping lock includes a projection. When the shipping lock is secured to the elongate body, the projection obstructs movement of the drive member to its advanced position.

In embodiments, the shipping lock is configured to prevent the tool assembly from pivoting relative to the body portion. The shipping lock may include a locking portion that engages the tool assembly to prevent pivoting of the tool assembly relative to the body portion. The tool assembly may include an anvil assembly and a cartridge assembly supporting a plurality of staples and the drive assembly is movable through the tool assembly to eject the plurality of staples from the cartridge assembly.

The drive assembly may include a clamping member. The projection may be positioned to obstruct movement of the clamping member towards the advanced position when the shipping lock is secured to the body portion. The clamping member may include an upper flange. The projection of the shipping lock may be positioned to engage the upper flange to obstruct movement of the drive member to the advanced position. The shipping lock may include curved arms configured to frictionally engage the elongate body.

BRIEF DESCRIPTION OF THE DRAWINGS

Various embodiments of the presently disclosed surgical stapler with small diameter endoscopic portion are described herein with reference to the drawings, wherein:

FIG. 3 is a first side perspective view of the stapler reload shown in FIG. 2;

FIG. 4 is a second side perspective view of the stapler reload shown in FIG. 2;

FIG. 19 is a perspective top view of the large diameter portion shown in FIG. 18, with a lockout assembly in a first or unlocked condition;

FIG. 20 is a cross-sectional view of the large diameter portion shown in FIG. 19, subsequent to actuation of the stapler reload;

FIG. 21 is a perspective top view of the large diameter portion shown in FIG. 19, subsequent to actuation of the stapler reload;

FIG. 22 is a perspective view of the large diameter portion shown in FIG. 21, during a second actuation of the stapler reload;

FIG. 23 is a perspective top view of a proximal portion of the large diameter portion shown in FIGS. 18-21, with a lockout member and lockout member tool shown in phantom;

FIG. 27 is a perspective view of a proximal portion of an inner body of the small diameter portion shown in FIG. 26;

FIG. 28 is a perspective view of the proximal portion of the inner body shown in FIG. 27, with the outer tube removed;

FIG. 29 is an enlarged perspective view of a pneumatic seal according to an embodiment of the present disclosure;

FIG. 45 is a side perspective view of a stapler reload according to another embodiment of the present disclosure including a shipping lock;

FIG. 46 is an enlarged side perspective view of a distal portion of the stapler reload and shipping lock shown in FIG. 45;

FIG. 48 is a cross-sectional view taken along section line 48-48 of FIG. 45;

FIG. 49 is a cross-sectional view taken along section line 49-49 of FIG. 48.

DETAILED DESCRIPTION OF EMBODIMENTS

Figure 1:
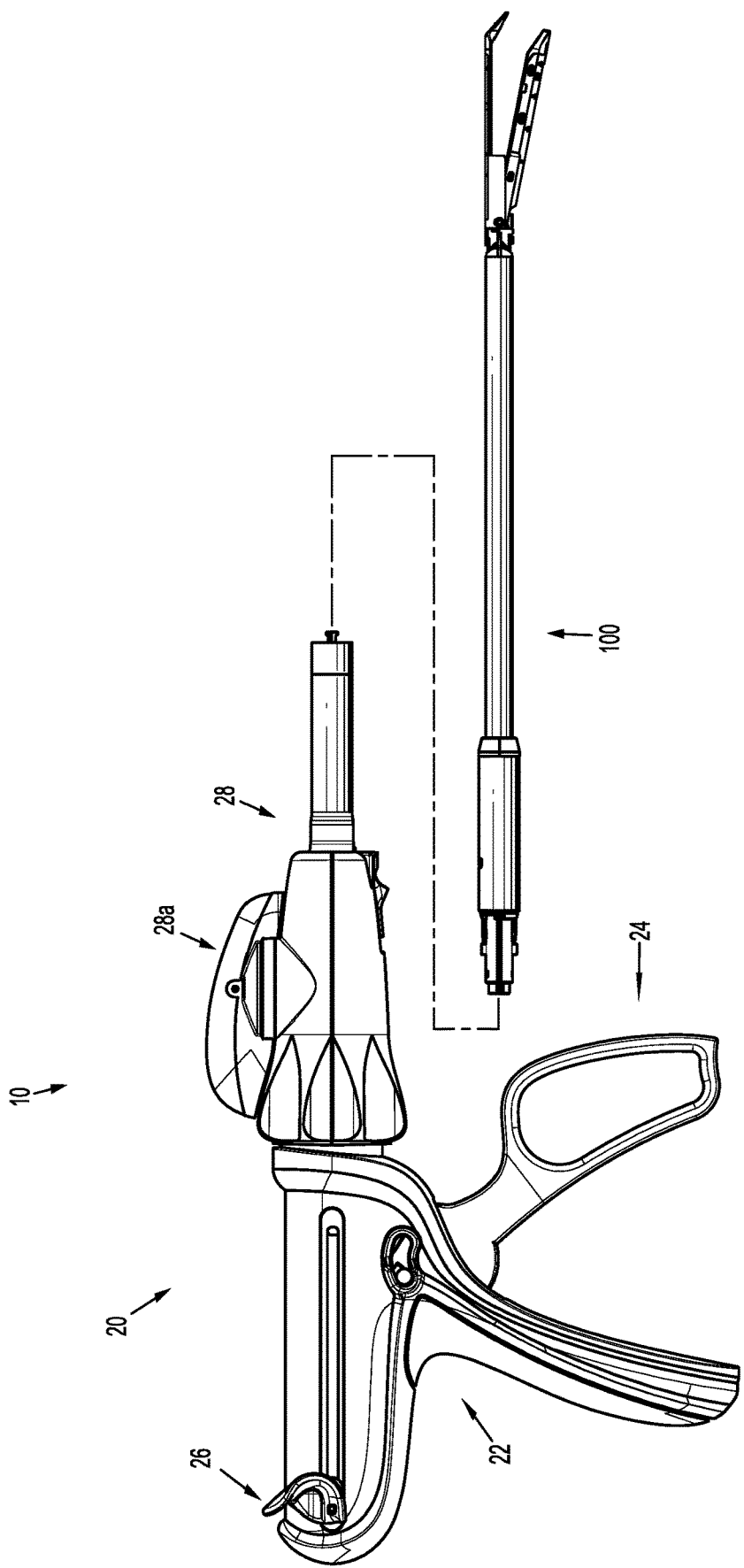
FIG. 1 is a side, perspective view of an embodiment of the presently disclosed surgical stapler with a small diameter endoscopic portion including a stapler reload and an adapter assembly secured to a handle assembly, with a tool assembly of the stapler reload in an open, non-articulated position.

Embodiments of the presently disclosed surgical stapler with a small diameter endoscopic portion will now be described in detail with reference to the drawings wherein like reference numerals designate identical or corresponding elements in each of the several views. In this description, the term "proximal" is used generally to refer to the portion of the apparatus that is closer to a clinician, while the term "distal" is used generally to refer to the portion of the stapler that is farther from the clinician. In addition, the term "endoscopic" is used generally to refer to surgical procedures performed through a small incision or a cannula inserted into a patient's body including endoscopic, laparoscopic and arthroscopic surgical procedures. Finally, the term clinician is used generally to refer to medical personnel including doctors, nurses, and support personnel.

FIG. 1 illustrates an embodiment of the presently disclosed small diameter reload is shown generally as stapler reload 100. The stapler reload 100 is part of a surgical stapling device 10 including a handle assembly or actuation device 20. In embodiments, the stapler reload 100 may be integrally formed with the handle assembly 20. As shown, the handle assembly 20 includes a handle 22, a trigger member 24 pivotally secured to the handle 22, and a pair of firing levers 26 (only one shown) extending from the handle 22, and an elongated body 28 rotatably secured to the handle 22 and including an articulating lever 28a. For a detailed description of an exemplary handle assembly, please refer to commonly owned U.S. Pat. No. 8,070,033, the content of which is incorporated herein by reference in its entirety.

Figure 2:
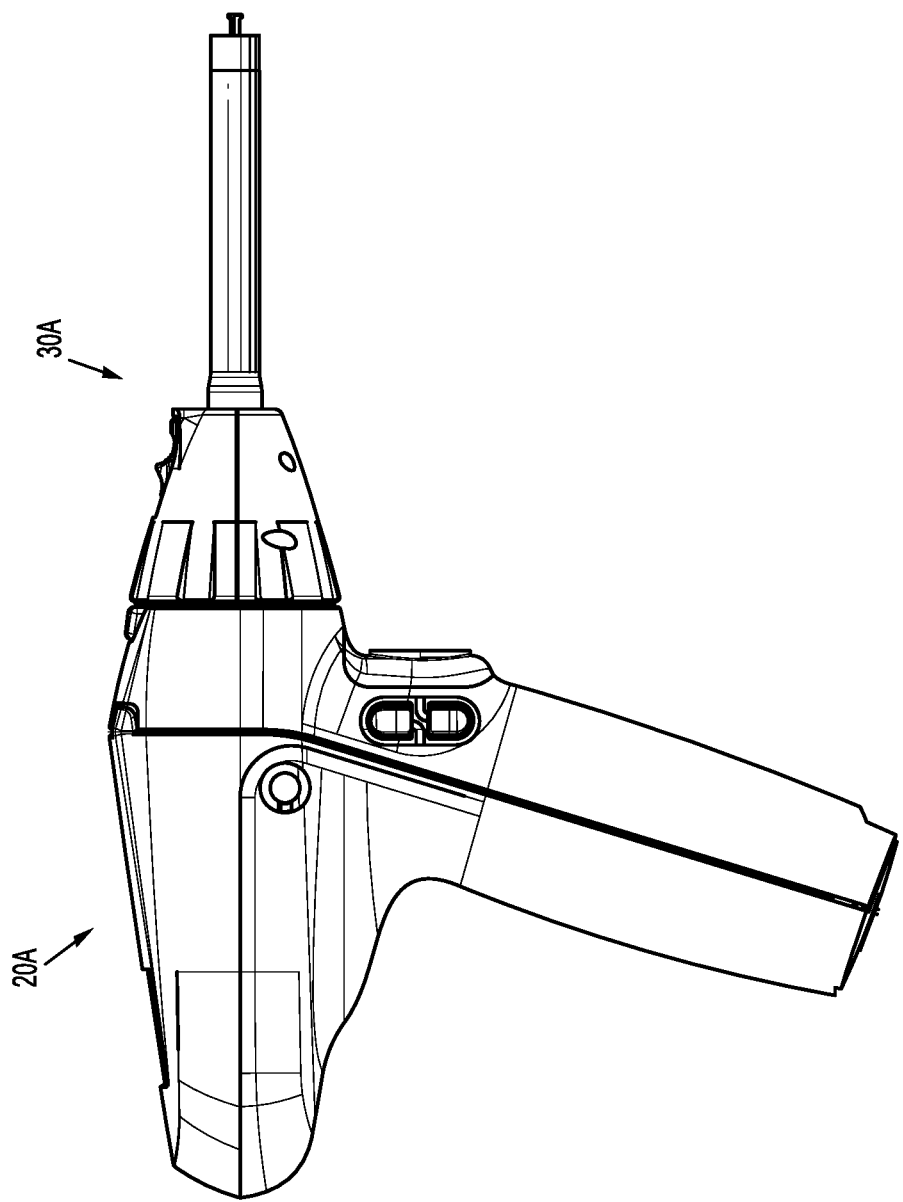
FIG. 2 is a side, perspective view of an adapter assembly secured to a powered actuation device for use with the stapler reload of FIG. 1.

Turning briefly to FIG. 2, it is envisioned that the stapler reload 100 may be operated with a powered handle assembly 20A. As shown, an adapter assembly 30A is secured to the powered handle assembly 20A and the stapler reload 100 is secured to the adapter assembly 30A. It is envisioned that the adapter assembly 30A and the stapler reload 100 (FIG. 1) and/or the handle assembly 20A can be integrally formed such that the stapler reload 100 is non-releasably supported on, or forms an integral extension of, the adapter assembly 30A and/or the handle assembly 20A. For a detailed description of exemplary handle assemblies and adapter assemblies, please refer to commonly owned U.S. Patent Application Publication No. 2012/0253329 ("the '329 publication"), the content of which is incorporated by reference herein in its entirety.

Referring to FIGS. 3 and 4, the stapler reload 100 includes a body portion 102, a mounting assembly 104, and a tool assembly 106. The body portion 102 defines a longitudinal axis "x" that is aligned with the longitudinal axis of the adapter assembly 30 (FIG. 1) and has a coupling portion 108, a large diameter portion 110, and an endoscopic or small diameter portion 112. The large diameter portion 110 of the stapler reload 100 has a diameter greater than the diameter of the small diameter portion 112. In embodiments, the small diameter portion 112 of the stapler reload 100 is dimensioned to be received in an 8 mm trocar assembly (not shown), whereas the large diameter portion 110 is about 12 mm in diameter and dimensioned to support a lock assembly 200 and a lockout assembly 220, as discussed in detail below.

Figure 39:
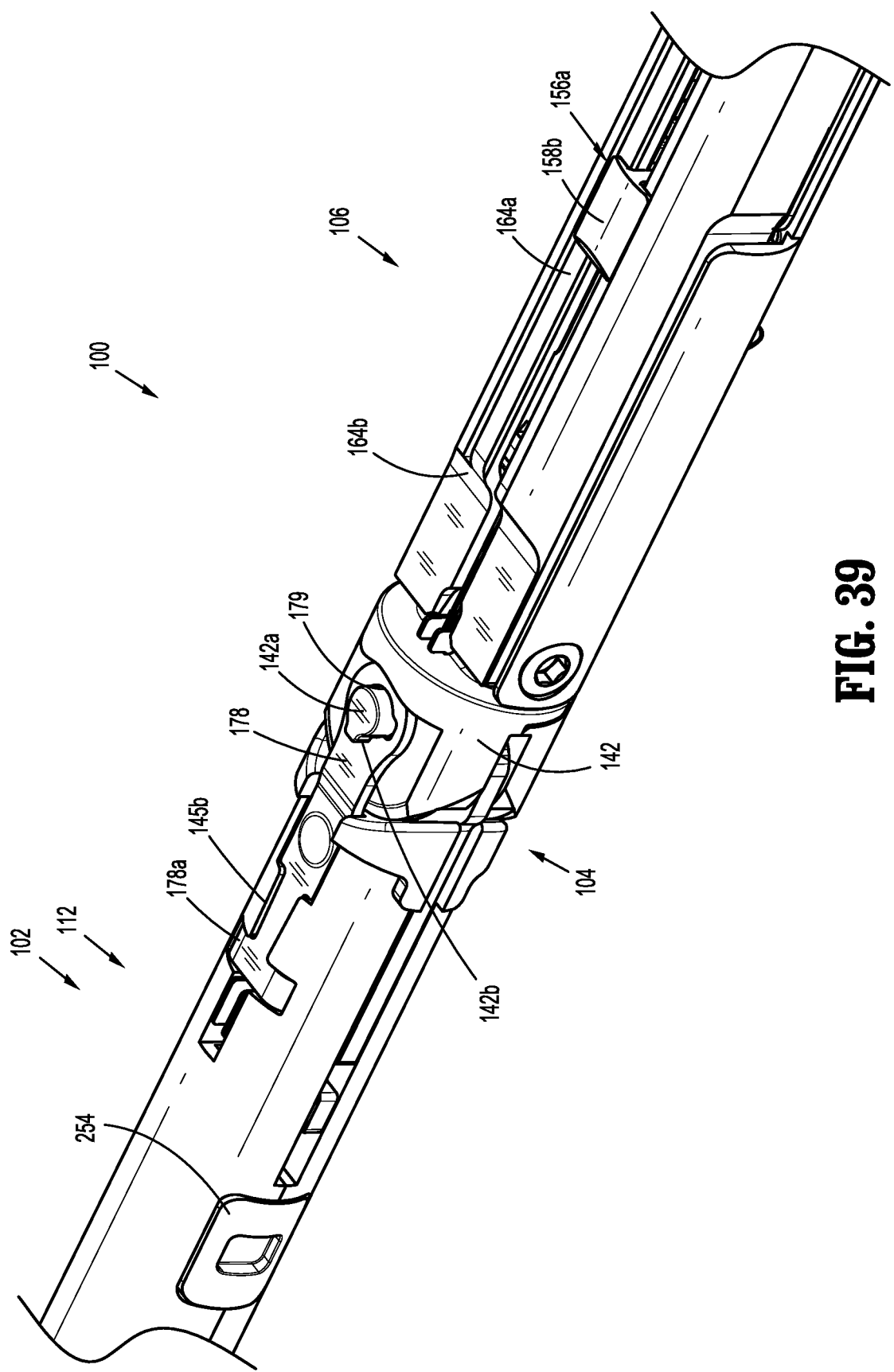
FIG. 39 is a perspective, side view of the articulating portion of the stapler reload shown in FIG. 30, with the outer tube of the body portion and the channel of the cartridge assembly removed.

The tool assembly 106 includes an anvil assembly 114 and a cartridge assembly 116. In embodiments, the cartridge assembly 116 is pivotally supported in relation to the anvil assembly 114 and is movable between an open position (FIG. 2) and a closed or approximated position (FIG. 39). Alternately, the anvil 114 can be pivotally coupled to the cartridge assembly 116. The mounting assembly 104 is supported on a distal portion of the body portion 102 and pivotally supports the tool assembly 106 to facilitate articulation of the tool assembly 106 about an axis perpendicular to the longitudinal axis "x" of the body portion 102 between an articulated position in which a longitudinal axis of the tool assembly 106 defines an acute angle with the longitudinal axis "x" of the body portion 102 and a non-articulated position in which the longitudinal axes of the tool assembly 106 and the body portion 102 are aligned.

Figure 5:
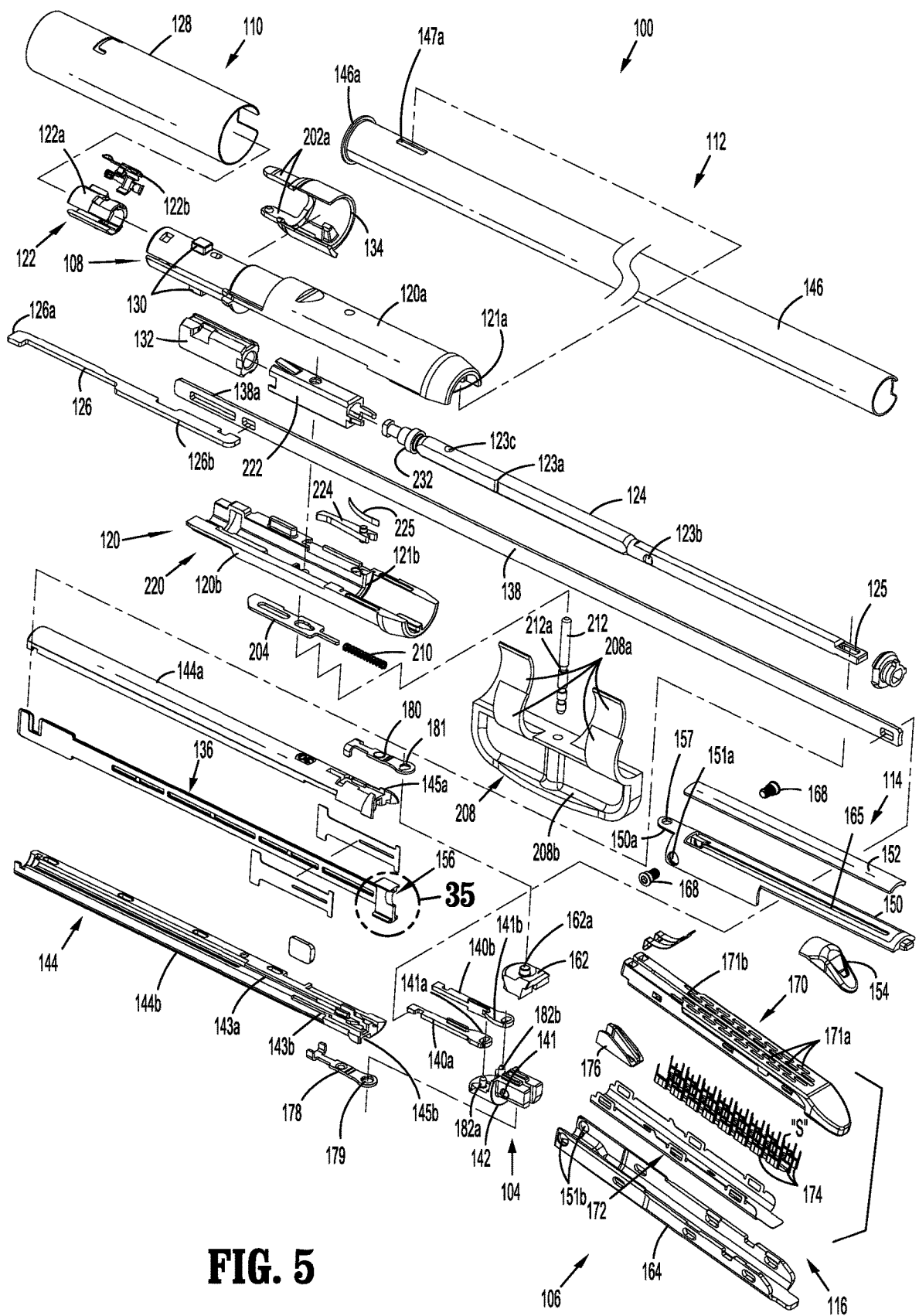
FIG. 5 is an exploded perspective view of the stapler reload shown in FIG. 2.
Figure 6:
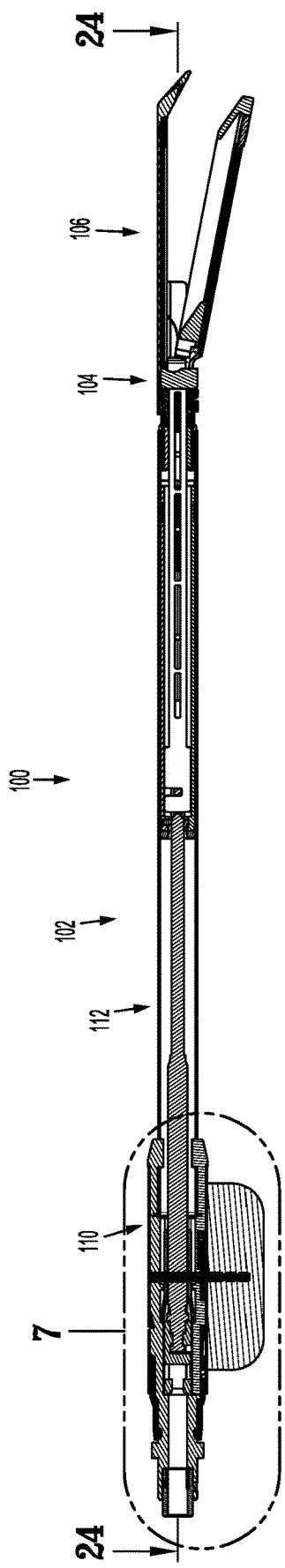
FIG. 6 is a cross-sectional view taken along section line 6-6 of FIG. 3.

Referring to FIG. 5, the large diameter portion 110 of the body portion 102 of the stapler reload 100 includes an inner housing 120 having an upper housing half-section 120a and a lower housing half-section 120b that are secured relative to each other with a tab and slot configuration as shown, or in any other suitable manner. The upper and lower housing half-sections 120a, 120b define channels 121a, 121b which slidably receive a drive member 124 and a first articulation link 126. The upper and lower housing half-sections 120a, 120b are received within a proximal body tube 128 that prevents separation of the half sections 120a, 120b.

The proximal portion of the upper housing half-section 120a defines the coupling portion 108 and includes engagement nubs 130 for releasably engaging the distal portion of the adapter assembly 30 (FIG. 1) in a bayonet-type coupling arrangement. For a detailed description of an exemplary coupling portion please refer to commonly owned U.S. Pat. No. 5,865,361 ("the '361 patent"), the content of which is incorporated herein by reference in its entirety.

An electrical connector assembly 122 is supported within the proximal portion of the upper housing half-section 120a of the body portion 102 of the stapler reload 100. The connector assembly 122 includes a connector base 122a and a contact member 122b. For a detailed discussion of an exemplary electrical connection assembly, please refer to commonly own U.S. Pat. App. Pub. No. 2016/0249929 ("the '929 application"), the content of which is incorporated by reference herein in its entirety.

The drive member 124 of the stapler reload 100 includes a proximal portion that supports a drive block 132. The drive block 132 is configured to releasably engage a control rod 32 (FIG. 2) of the adapter assembly 30 (FIG. 2) to translate movement of the control rod 32 into movement of the drive member 124. The drive block 132 is operably engaged by a locking sleeve 134 to prevent firing of the stapler reload 100 prior to the stapler reload 100 being properly secured to adapter assembly 20 (FIG. 1). A distal portion of the drive member 124 defines a slot 125 that engages a hooked proximal portion of a drive assembly 136 such that distal movement of the drive member 124 effects distal movement of the drive assembly 136.

By providing the stapler reload 100 with a large diameter portion 110 for housing the drive block 132 and the locking sleeve 134, as well as other components of the stapler 10 described below, the diameter of the small diameter portion 112 can be minimized, for example, to about 8 mm such that it may be received within an 8 mm trocar assembly (not shown), while the large diameter portion 110 may be about 12 mm in diameter or larger.

Referring still to FIG. 5, the first articulation link 126 defines a hooked proximal portion 126a that is configured to engage an articulation shaft (not shown) of the adapter assembly 30 (FIG. 1) when the stapler reload 100 is secured to the adapter assembly 30. A distal portion 126b of the first articulation link 126 engages a proximal portion 138a of a second articulation link 138. Although shown having a hook and notch configuration and a corresponding slotted configuration, the respective distal portion 126b of the first articulation link 126 and the proximal portion 138a of the second articulation link 138 may be secured to one another in any suitable manner.

The proximal portion 138a of the second articulation link 138 is slidably positioned within the large diameter portion 110 of the body portion 102 of the stapler reload 100. The distal portion 138b of the second articulation link 138 engages a first articulation member 140a which is pivotally connected to a lower mounting bracket 142 of the mounting assembly 104 at a location offset from the longitudinal axis of the body portion 102 such that longitudinal movement of the second articulation link 138 effects pivotal movement of the tool assembly 106 about the longitudinal axis.

The small diameter portion 112 of the body portion 102 of the stapler reload 100 includes an inner body 144 having upper and lower half-sections 144a, 144b that are received within an outer tube 146. The upper and lower half-sections 144a, 144b define a first channel 143a that slideably receives the drive member 124 and the drive assembly 136. The upper and lower half-sections 144a, 144b also define a second channel 143b that slideably receives the second articulation link 138. Respective distal ends of the upper and lower half-sections 144a, 144b also define cutouts 145a, 145b. The outer tube 146 includes a proximal flange 146a for securing the outer tube 146 to the upper and lower housing half-section 120a, 120b of the large diameter portion 110 of the body portion 102. The outer tube 146 defines openings 147a, 147b (FIG. 20) for receiving respective protrusions 230a, 230b (FIG. 20) of respective upper and lower housing half-sections 120a, 120b.

As noted above, the tool assembly 106 includes the anvil assembly 114 and the cartridge assembly 116. The anvil assembly 114 includes an anvil body 150 and an anvil cover 152 which is secured to the topside of the anvil body 150 to define a channel (not shown). In embodiments, staple pockets 151 are formed directly into the anvil body 150. Alternatively, the anvil body 150 may be provided with an anvil plate (not shown). In embodiments, the anvil body 150 may be one-piece, e.g., monolithic. In embodiments, the staple pockets may be formed using micro-electrolytic dissolution (MED). In embodiments, the anvil body 150 may include a lubricated hard coating.

Figure 37:
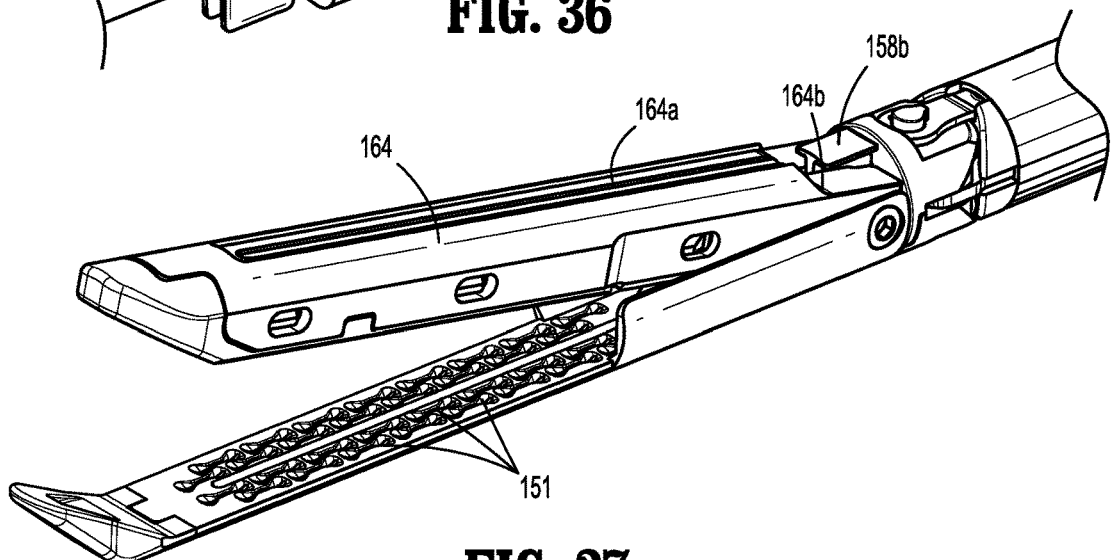
FIG. 37 is a perspective view of the tool assembly the stapler reload shown in FIGS. 1 and 2.

In embodiments, a dissector tip 154 is supported on the distal portion of the anvil body 150. The anvil body 150 defines plurality of staple receiving depressions 151 (FIG. 37) and a longitudinal slot 153 which is dimensioned to slideably receive a portion of a working portion 156 of the drive assembly 136 of the stapler reload 100. A proximal portion of the anvil body 150 includes a bracket 150a defining a hole 157 for receiving a pivot member or boss 162a of an upper mounting bracket 162 of the mounting assembly 104.

In embodiments, the tissue dissector 154 is secured to a distal portion of the anvil assembly 114 with friction fit, adhesives, welding, mechanical fasteners, or in any suitable manner. The tissue dissector 154 has a tapered configuration and extends distally of the distal portion of the cartridge assembly 116 to allow the tool assembly 106 to be manipulated about tissue adjacent a surgical site. The tissue dissector 154 may be attached to the distal portion of the anvil assembly 114, as shown, or may be integrally and/or monolithically formed with the anvil assembly 114. Alternately, the tissue dissector 154 may be attached to the cartridge assembly 116. In addition, the anvil assembly 114 may include a buttress material (not shown) to strengthen tissue being sutured and dissected as is known in the art.

In some embodiments, the cartridge assembly 116 includes a channel 164 and a staple cartridge 166 that is received within the channel 164. It is envisioned that the staple cartridge 166 may be attachable to the channel 164 by a snap-fit connection, or in any suitable manner, and may be removable to permit replacement following a stapling procedure. For a detailed description of an exemplary replaceable staple cartridge assembly, please refer commonly owned U.S. Pat. App. Pub. No. 2012/0286021 ("the '021 publication"), the content of which is incorporated herein by reference in its entirety.

The channel 164 is pivotally secured to the anvil body 150 by pivot pins 168 which extend through openings 151a formed in the anvil body 150 and openings 151b formed in the channel 164. The staple cartridge 166 includes a cartridge body 170 which may define only two rows of staple retention slots 171a on each side of a knife slot 171b to facilitate reduction in the diameter of the tool assembly 106. The knife slot 171b is aligned with an elongated slot 165 defined in the channel 164 to facilitate passage of a dynamic clamping member 156a. The staple retention slots 171a are positioned along a tissue contact surface of the cartridge body 170 and are aligned with the staple forming depressions 151 (FIG. 37) of the anvil body 150. Each staple retention slot 171a is configured to receive a fastener or staple "S" and a pusher 174. A cartridge shield 172 allows the pushers 174 to float, and prevents the pushers 174 from exiting a respective staple retention slot 171a during transport and prior to use. An actuation sled 176 is positioned to pass longitudinally through the cartridge body 170 into engagement with the pushers 174 to sequentially eject the staples "S" from the cartridge body 170. For a detailed description of an exemplary cartridge assembly, please refer to commonly owned U.S. Pat. App. Pub. No. 2013/0098965 ("the '965 publication"), the content of which is incorporated by reference herein in its entirety.

Figure 33:
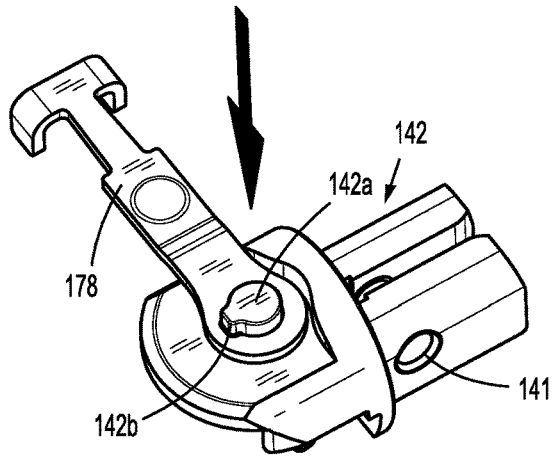
FIG. 33 is a perspective view of the coupling member and upper mounting bracket shown in FIG. 32, prior to locking the coupling member to the upper mounting bracket.
Figure 34:
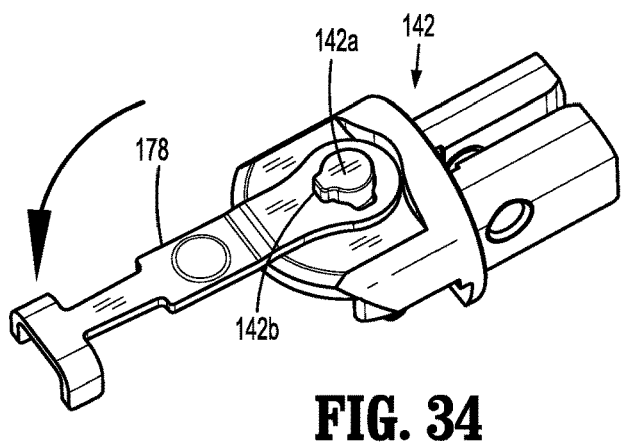
FIG. 34 is a perspective view of the coupling member and upper mounting bracket shown in FIGS. 32 and 33, subsequent to locking the coupling member to the upper mounting bracket.

The mounting assembly 104 includes the upper mounting bracket 162 and the lower mounting member 142. Each of the upper and lower mounting brackets 162, 142 includes a pivot member or boss 162a, 142a (FIG. 33), respectively. As discussed above, the pivot member 162a is received within the hole 157 of the bracket 150a of the anvil body 150 to secure the upper mounting bracket 162 to the anvil body 150. A first coupling member 178 has a first portion which defines an opening 179 that also receives the pivot member 162a and a second portion which is received within the cutout 145a defined in the distal portion of the upper half-section 144a of the small diameter portion 112 of the body portion 102 of the stapler reload 100. The pivot member 142a on the lower mounting bracket 142 is received in an opening 181 defined in a first portion of a second coupling member 180. The second coupling member 180 has a second portion that is received within the cutout 145b defined within lower housing half-section 144b of the body portion 102 to pivotally secure the lower mounting bracket 142 to the lower housing half-section 144b of the inner body 140 of the body portion 102 of the stapler reload 100.

The pivot pins 168 extend through openings 151a formed in the anvil body 150 and openings 151b formed in the channel 164, and are received in openings 141 formed in lower mounting bracket 142 to secure the lower mounting bracket 142 to the channel 164. The upper and lower mounting brackets 162, 142 are secured together by pin members 182a, 182b.

Referring to FIGS. 5-13, a lock assembly 200 is supported on the proximal portion of large diameter portion 110 of the body portion 102 of the stapler reload 100 to prevent axial movement of the drive assembly 136 until the stapler reload 100 is properly attached to the adapter assembly 30 (FIG. 1) of the surgical stapler 10 (FIG. 1). The lock assembly 200 includes the drive block 132 supported on the proximal portion of the drive member 124 and the rotatable sleeve 134 is configured for selective engagement with the drive block 132 to prevent longitudinal movement of the drive member 124. The rotatable sleeve 134 is mounted about the proximal portion of the housing 120 of the body portion 102, and includes two proximally extending fingers 202a. The rotatable sleeve 134 also includes a distally extending flange 202b. A lock plate 204 is slideably supported within a cutout 201a of the lower housing half-section 120b of the inner housing 120 of the body portion 102 of the stapler reload 100, and is positioned to be engaged by the distally extending flange 202b of the rotatable sleeve 134 during attachment of the stapler reload 100 to the adapter assembly 30 (FIG. 1) to prevent forward movement of the drive member 124.

The rotatable sleeve 134 also includes a blocking finger 202c that extends downwardly into the path of the drive block 132 to obstruct movement of the drive block 132 when the rotatable sleeve 134 is in a first or locked position. When the rotatable sleeve 134 is rotated, as indicated by arrow "A" in FIGS. 11 and 13, the blocking finger 202c is moved from the first position (FIG. 8) in engagement with the drive block 132 to a second position (FIG. 11) spaced from the drive block 132 to facilitate longitudinal movement of the drive block 132 and, thus, drive member 124.

Figure 7:
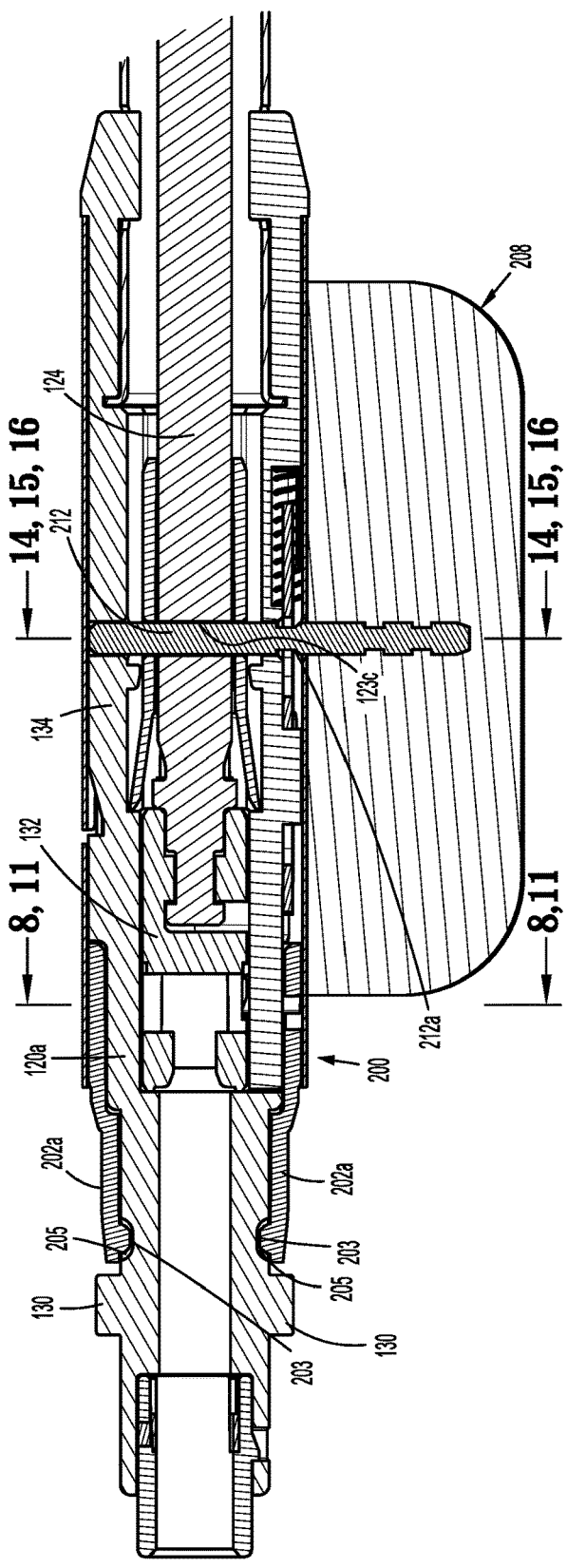
FIG. 7 is an enlarged view of the indicated area of detail shown in FIG. 6.
Figure 8:
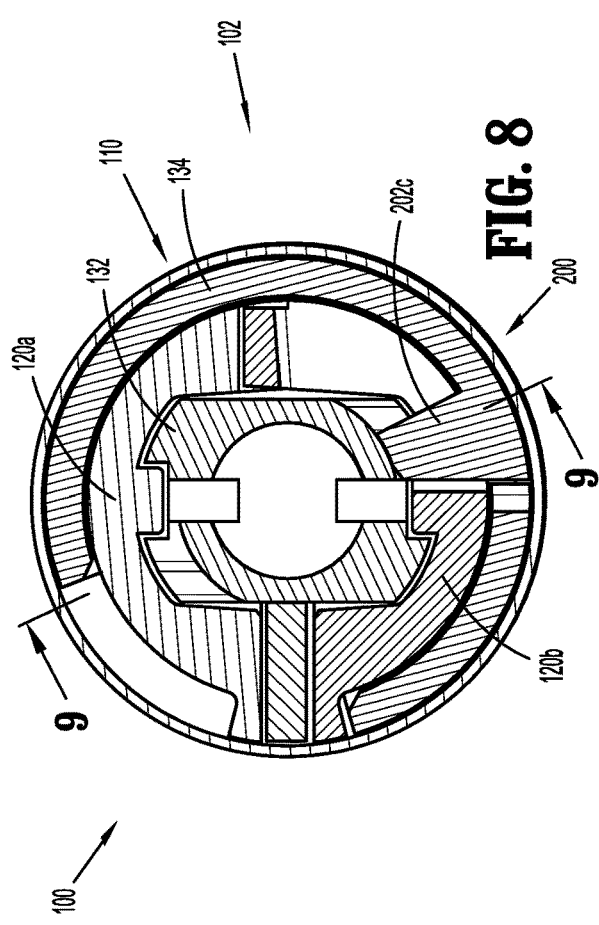
FIG. 8 is a cross-sectional view taken along section line 8-8 of FIG. 7.
Figure 9:
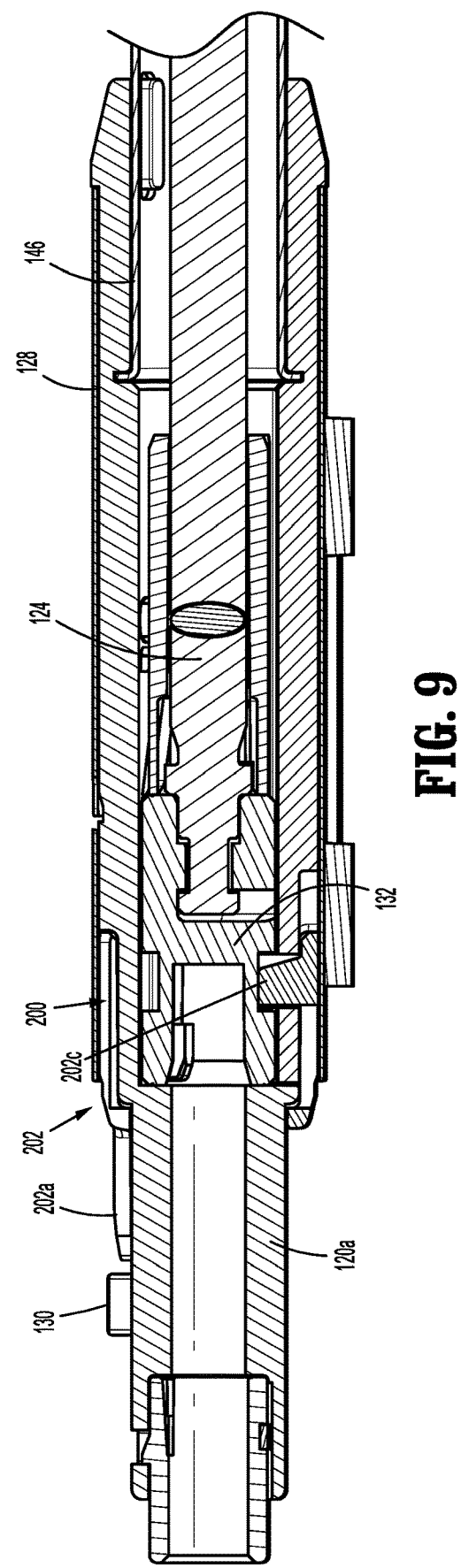
FIG. 9 is a cross-sectional view taken along section line 9-9 of FIG. 8.
Figure 10:
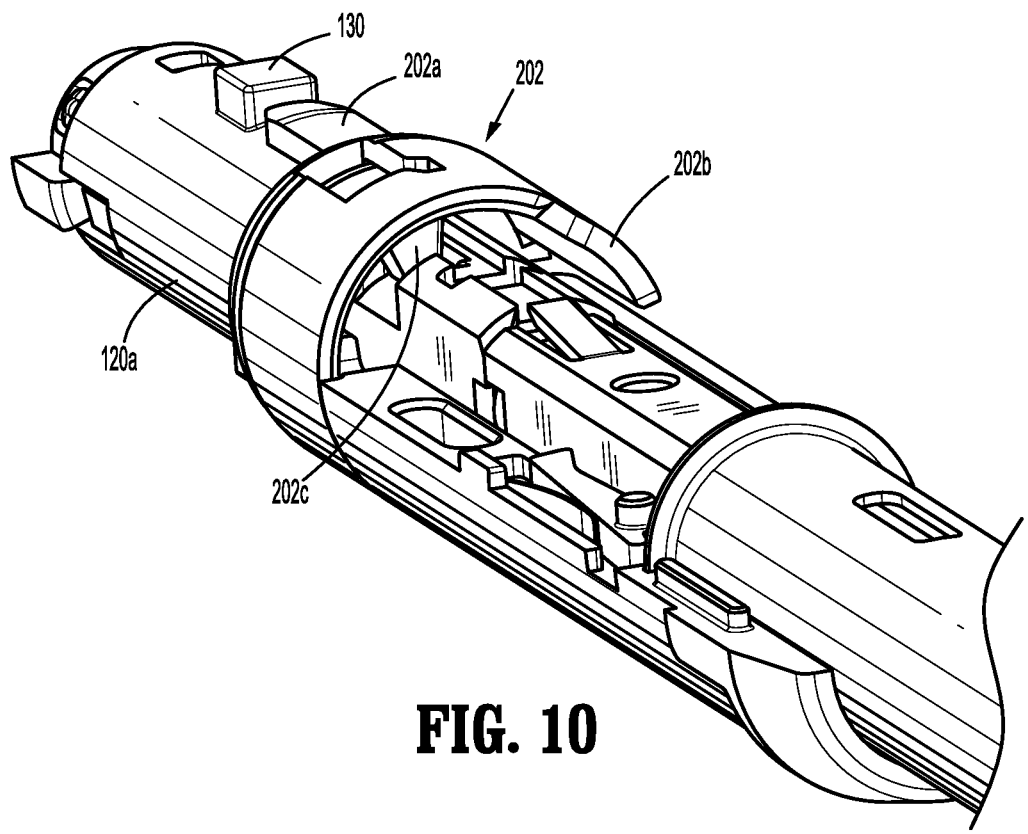
FIG. 10 is a perspective view of a large diameter portion of a body portion of the stapler reload of FIG. 1, with an upper half-section removed and a rotatable sleeve in a first or locked position.
Figure 11:
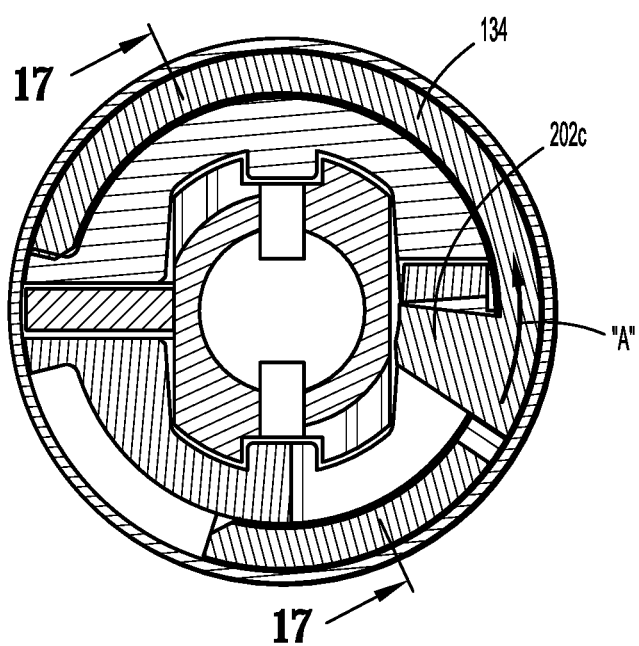
FIG. 11 is a cross-sectional view taken along section line 11-11 of FIG. 7.

With particular reference to FIG. 7, when the rotatable sleeve 134 is positioned about the proximal portion of the lower housing half-section 120b, the proximally extending fingers 202a of the locking sleeve 134 are positioned in alignment with the nubs 130 on the upper housing half-section 120a. Each proximally extending finger 202a includes an inwardly extending protrusion 203 that is received in a respective recess 205 formed on an outer surface of the upper half section 120a to releasably retain the sleeve 134 in the first position. When the stapler reload 100 is attached to an adapter assembly 30 (FIG. 1), the proximal portion of the stapler reload 100 is inserted into the distal portion of the adapter assembly 30 (FIG. 1) and rotated to engage the bayonet-type coupling components of the stapler reload 100 and the adapter assembly 30. As the adapter assembly 30 is rotated in relation to the stapler reload 100, a portion of the adapter assembly 30 engages the proximally extending fingers 202a of the rotatable sleeve 134 to rotate the rotatable sleeve 134 about the inner housing 120 of the stapler reload 100 from the first position (FIG. 8) to the second position (FIG. 11).

The stapler reload 100 is provided with a shipping lock 208 configured to prevent operation of the stapler reload 100. The shipping lock 208 is selectively secured to the large diameter portion 110 of the body portion 102 of the stapler reload 100 and extends through an opening 123c in the drive member 124 to prevent axial movement of the drive member 124. The shipping lock 208 is configured to be separated from the body portion 102 of the stapler reload 100 only after the stapler reload 100 is properly secured to an actuation device 20 (FIG. 1).

Figure 12:
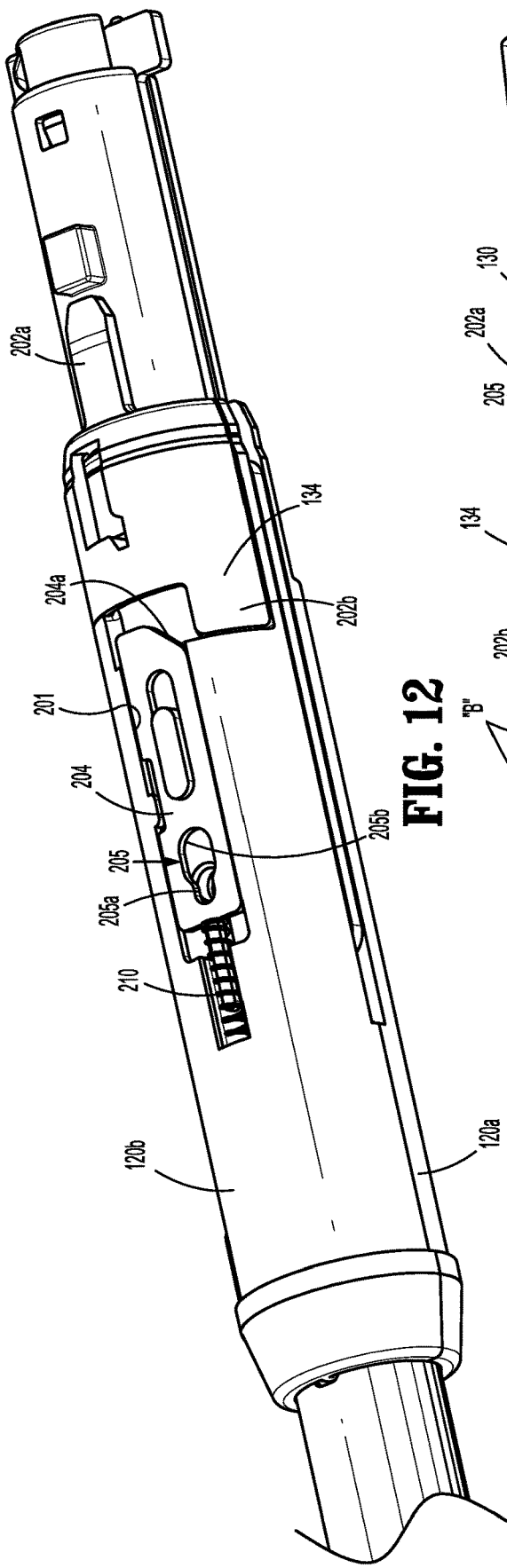
FIG. 12 is a side perspective view of the large diameter portion shown in FIG. 10 with an outer tube removed and the rotatable sleeve in the first position.
Figure 13:
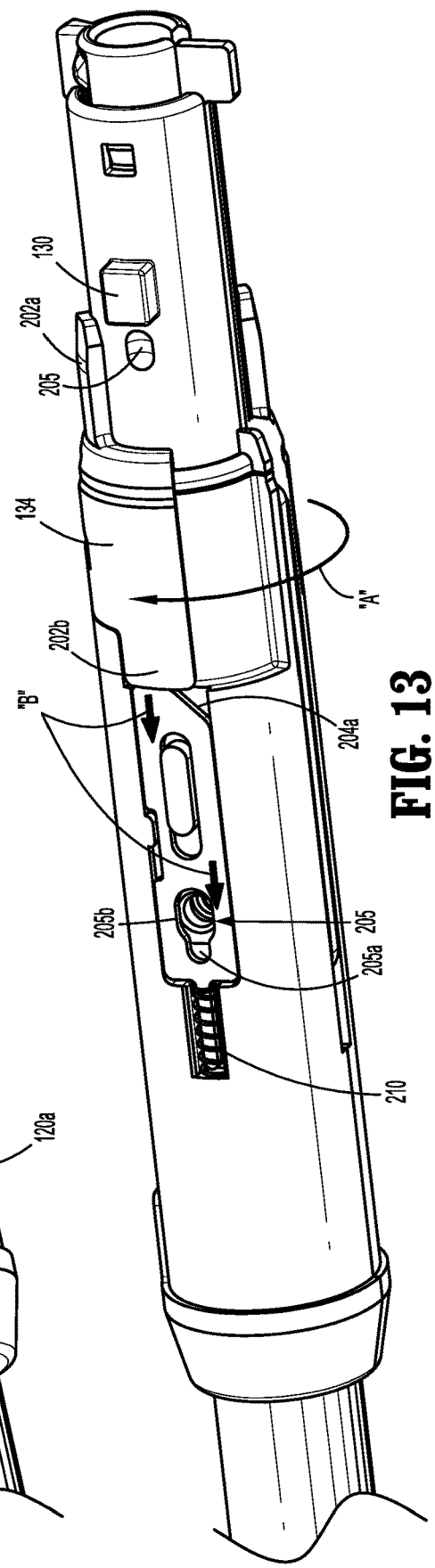
FIG. 13 is a side perspective view of the large diameter portion shown in FIG. 10 with the outer tube removed and the rotatable sleeve in a second or unlocked position.

As noted above, rotation of the rotatable sleeve 134 from the first position to the second position also causes the distally extending flange 202b of the rotatable sleeve 134 to engage the lock plate 204. With particular reference to FIGS. 12 and 13, the lock plate 204 is received within the cutout 201 of the lower housing half-section 120b and is configured to prevent release of the shipping lock 208 (FIG. 7) from engagement with the body portion 102 of the staple reload 100 until the staple reload 100 is properly secured to the adapter assembly 30 (FIG. 1). More particularly, the lock plate 204 is biased proximally by a spring 210 and defines a lock slot 205 for releasably engaging a locking pin 212 of the shipping lock 208. The lock slot 205 includes a small diameter portion 205a sized to be received around a notched portion 212a (FIG. 7) of the locking pin 212 of the shipping lock 208, and a large diameter portion 205b through which the entirety of the locking pin 212 can be received.

During rotation of the rotatable sleeve 132, the distally extending flange 206 of the rotatable sleeve 134 engages a cammed surface 204a of the lock plate 204, causing the lock plate 204 to move in the distal direction, as indicated by arrows "B" in FIG. 13, against the bias of the spring 210. As the lock plate 204 moves from a proximal position (FIG. 12) to a distal position (FIG. 13), the lock slot 205 is moved from having the small diameter portion 205a positioned about the notched portion 212a of the locking pin 212 to having the large diameter portion 205b received about the locking pin 212. With the notched portion 212a of the locking pin 212 positioned within the large diameter portion 205b, the locking pin 212 can be withdrawn from the stapler reload 100. In this manner, distal movement of the lock plate 204 permits release of the locking pin 212 of the shipping lock 208 from engagement with the stapler reload 100.

Figure 14:
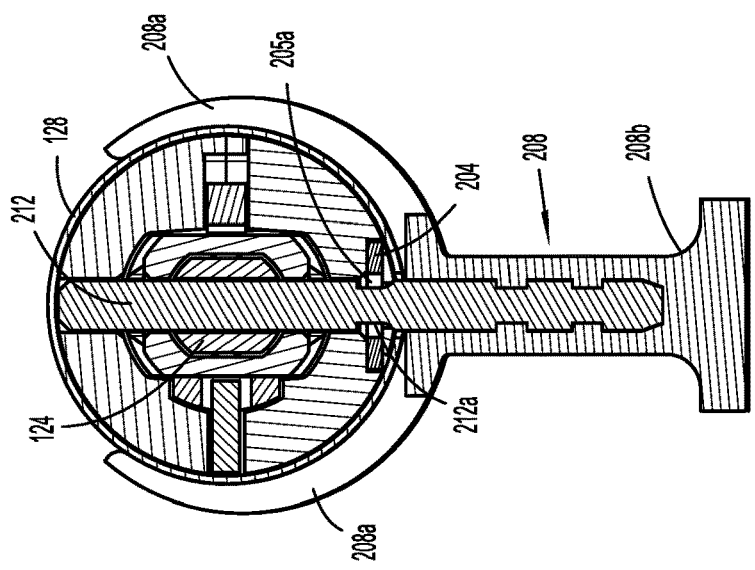
FIG. 14 is a cross-sectional view taken along section line 14-14 of FIG. 7, with a locking member in a proximal position and a shipping lock secured to the body portion of the stapler reload.

Turning now to FIG. 14, the shipping lock 208 is shown secured to the large diameter portion 110 of the body portion 102 of the stapler reload 100. In particular, curved arms 208a of the shipping lock 208 are received about proximal body tube 128 of the large diameter portion 110 of the body portion 102 and the locking pin 212 is received through openings in the upper and lower housing half-sections 120a, 120b of the housing 120, and through openings in a lockout shield 222 and the drive member 124. In this manner, the drive member 124 is prevented from longitudinal movement in any direction. The notched portion 212a of the locking pin 212 is engaged by the lock plate 204 to prevent the shipping lock 208 from accidentally disengaging from the stapler reload 100 prior to the staple reload 100 being properly secured to the adapter assembly 30 (FIG. 1).

Figure 15:
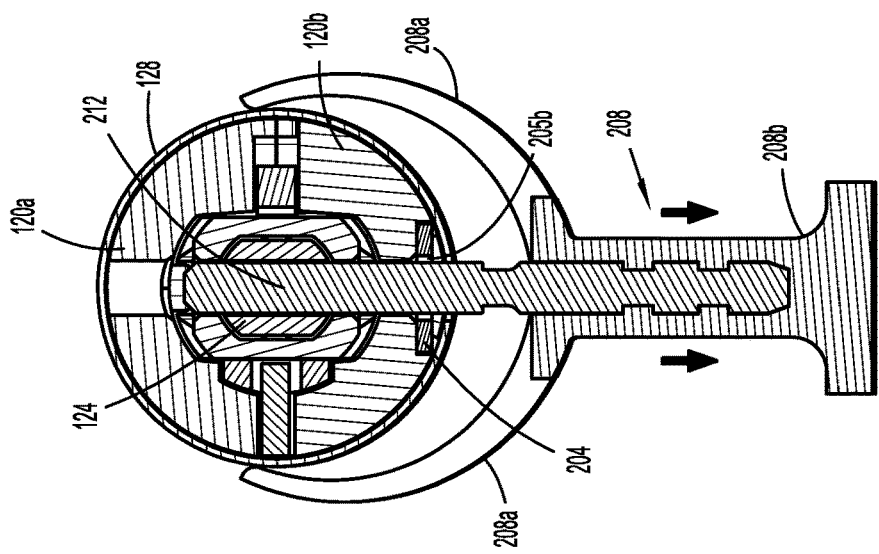
FIG. 15 is a cross-sectional view taken along section line 15-15 shown in FIG. 7, with the locking member in a distal position as the shipping lock is being released from the body portion of the stapler reload.

With reference now to FIG. 15, during rotation of the rotatable sleeve 134 during attachment of the stapler reload 100 to the adapter assembly 30 (FIG. 1), the lock plate 204 is moved distally via engagement with the flange 202b of rotatable sleeve 134 (FIG. 13) to align the large portion 205b of the lock slot 205 with the locking pin 212 of the shipping lock 208. In this manner, the locking plate 204 is disengaged from within the locking pin 212 such that the locking pin 212 is no longer secured to the body portion 102 of the stapler reload 100, and the shipping lock 208 is free to be separated from the body portion 102 of the stapler reload 100. A handle portion 208b of the shipping lock 208 is configured to be grasped and facilitate separation of the shipping lock 208 from the body portion 102. More particularly, the handle portion 208b permits a user to pull the shipping lock 208 radially outward from the body portion 102 of the stapler reload 100 to overcome the spring force of the arms 208a of the shipping lock 208 to release the shipping lock 208 from the body portion 102 of the stapler reload.

Figure 16:
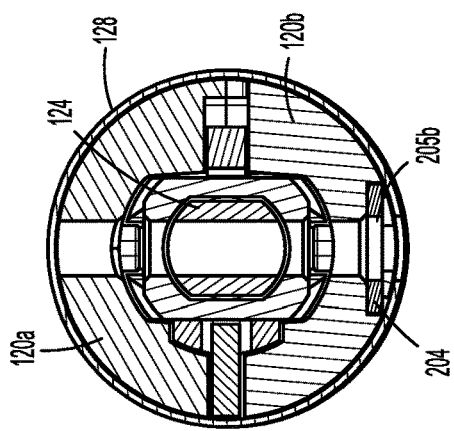
FIG. 16 is a cross-sectional view taken along section line 16-16 shown in FIG. 7, with the shipping lock removed.

Turning briefly to FIG. 16, once the shipping lock 208 (FIG. 15) is separated from the stapler reload 100, the stapler reload 100 is ready for use.

Figure 17:
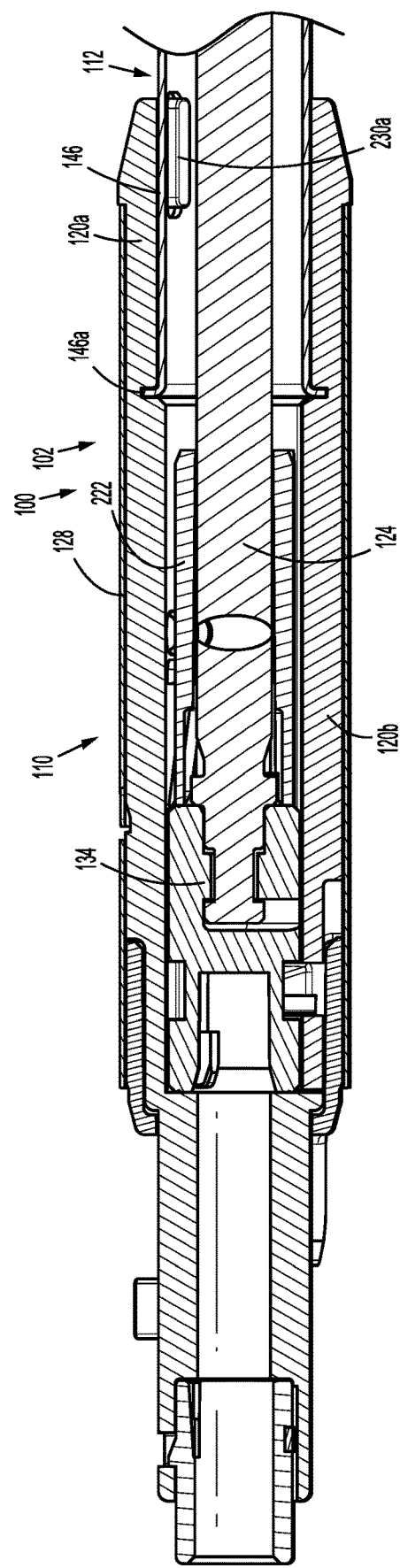
FIG. 17 is a cross-sectional view taken along section line 17-17 shown in FIG. 11.
Figure 18:
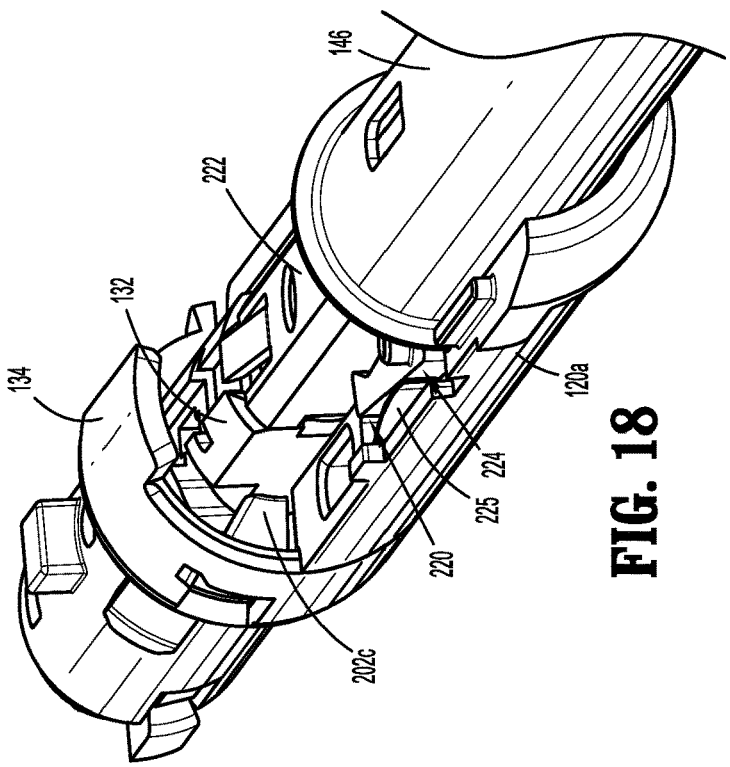
FIG. 18 is a perspective view of the large diameter portion shown in FIG. 10, with the upper half-section removed and the rotatable sleeve in the second position.

With reference now to FIGS. 5 and 18-23, the large diameter portion 110 of the body portion 102 of the stapler reload 100 includes a lockout assembly 220 to prevent subsequent advancement of the drive member 124 following firing of the stapler reload 100. The lockout assembly 220 includes a lockout shield 222 and a lockout member 224. The lockout shield 222 is slideably disposed about a proximal portion of the drive member 124 and includes a pair of proximally extending and outwardly biased shield lances 226a (FIGS. 19 and 20) and a pair of distally extending shield fingers 226b. The shield lances 226a operate to prevent retraction of the lockout shield 222 subsequent to actuation of the stapler reload 100. The shield fingers 226b engage a proximal set of notches 123a (FIG. 5) of the drive member 124 prior to actuation of the stapler reload 100, i.e., before the lockout shield 222 is moved distally (FIG. 17), to maintain the lockout shield 222 in engagement with the drive block 132. Subsequent to advancement of the drive block 132 and the lockout shield 222 (FIG. 21), the shield fingers 226b engage a distal set of notches 123b (FIG. 5) in the drive member 124 (FIG. 17) to assist in retaining the drive member 124 subsequent to retraction of the drive member 134.

With particular reference to FIGS. 19 and 21, the lockout member 224 is pivotally supported within the inner housing 120 of the body portion 102 and includes a proximal portion 224a that is biased radially inward by a spring member, e.g., leaf spring 225, into engagement with the lockout shield 222 prior to firing of the stapler reload 100 (FIG. 26) and into engagement with the drive member 124 subsequent to retraction of the drive member 124 following actuation of the stapler reload 100.

With particular reference to FIG. 20, during actuation of the stapler reload 100, engagement of the drive block 132 by the connector rod 32 (FIG. 2) of the adapter assembly 30 (FIG. 2) causes the drive member 124 and the lockout shield 222 to advance distally, as indicated by arrows "C" in FIG. 20. As the drive block 132 is advanced, the lockout shield 222 is moved distally into the outer tube 146 of the small diameter portion 112 of the body portion 102 of the stapler reload 100. Once the lockout shield 222 is received within the outer tube 146, the shield lances 226a of the lockout shield 222 engage protrusions 230a, 230b formed on respective upper and lower housing half-sections 120a, 120b of housing 120. Engagement of the shield lances 226a with the protrusion 230a, 230b of the respective upper and lower housing half-sections 120a, 120b prevents proximal movement of the lockout shield 222 as the drive member 124 is retracted to its initial position subsequent to the actuation stroke.

With particular reference now to FIG. 21, when the drive member 124 returns to its initial position, subsequent to the actuation stroke of the stapler reload 100, as noted above, the lockout shield 222 remains within the outer tube 146 of the small diameter portion 110 of the body portion 102 of the stapler reload 100 because of the shield lances 226a of the lockout shield 222 prevent proximal movement of the lockout shield 222. Without the lockout shield 222 being received around the proximal portion of the drive member 124, the proximal portion 224a of the lockout member 224 directly engages the drive member 124. During any subsequent attempted actuations of the stapler reload 100 after the initial actuation, the proximal portion 224a of the lockout member 224 will engage a flange 232 located distal of the proximal portion of the drive member 124, thereby preventing further distal movement of the drive member 124.

As shown in FIG. 23, a lockout reset opening 229 is provided in the housing 120 of the body portion 102 of the stapler reload 100 to permit overriding of the lockout assembly 220. In particular, a tool, e.g., screw driver 234, may be received through the lockout reset opening 229 and engaged with a distal portion 224b of the lockout member 224, as indicated by arrow "D", to pivot the proximal portion 224a of the lockout member 224 from engagement with the flange 232 (FIG. 22) of the drive member 124, as indicated by arrow "E".

Figure 24:
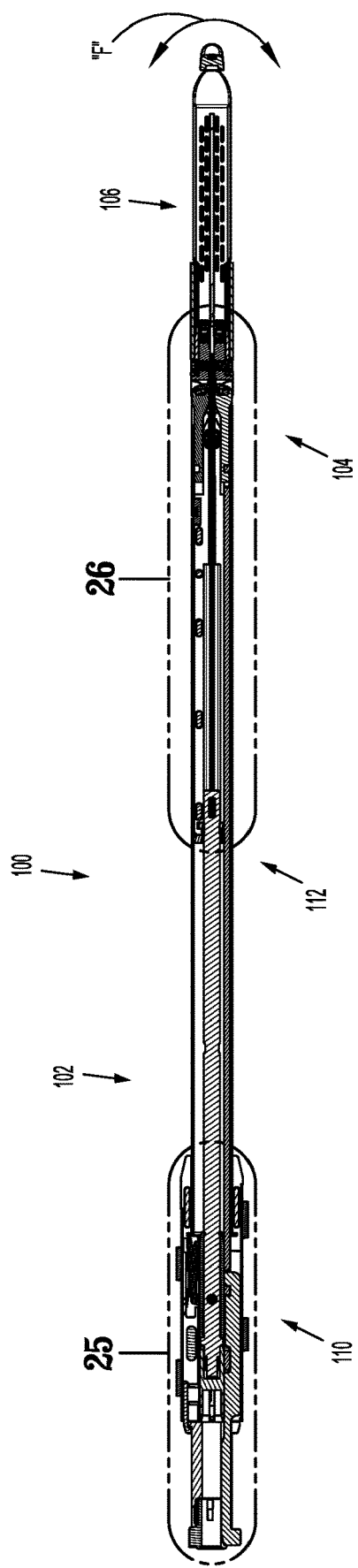
FIG. 24 is a cross-sectional top view of the stapler reload shown in FIGS. 1 and 2.
Figure 25:
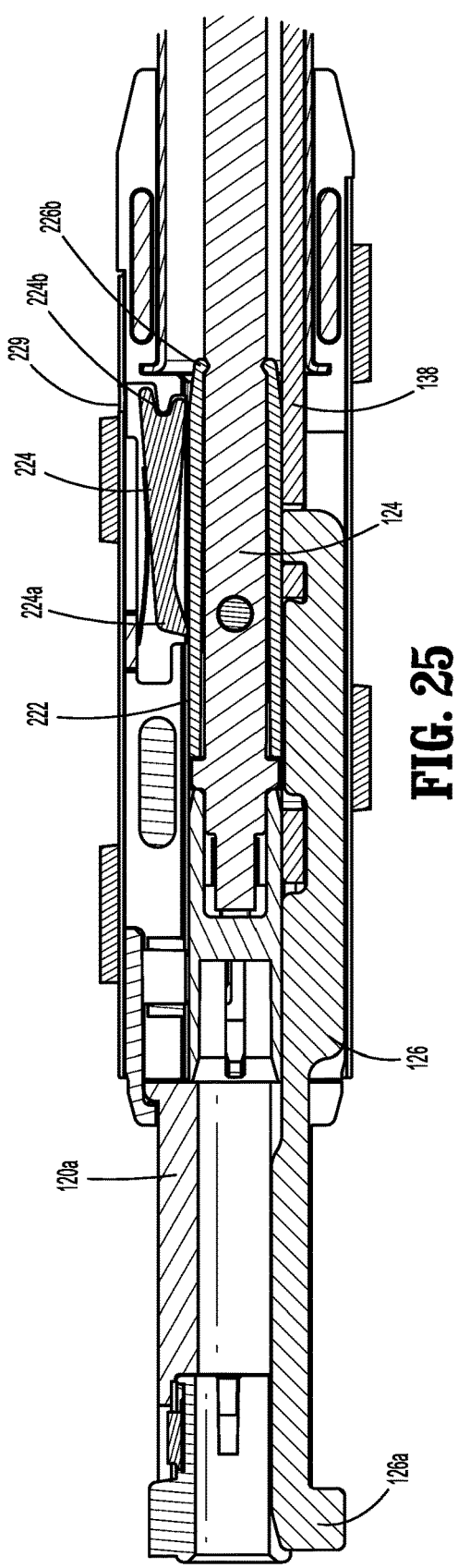
FIG. 25 is a cross-sectional top view of the large diameter portion shown in FIGS. 18-21, prior to actuation of the stapler reload.
Figure 26:
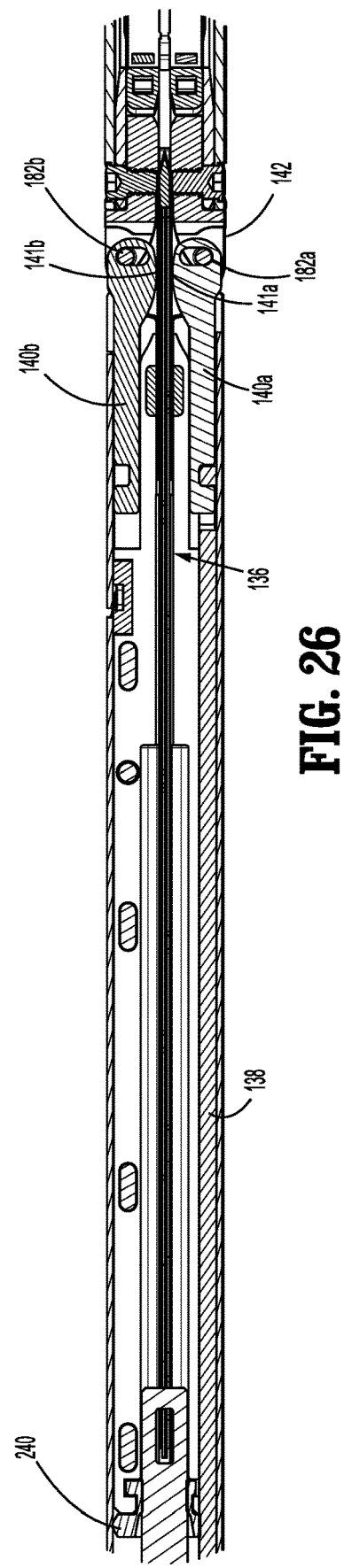
FIG. 26 is a cross-sectional top view of a small diameter portion of the stapler reload shown in FIGS. 1 and 2.
Figure 30:
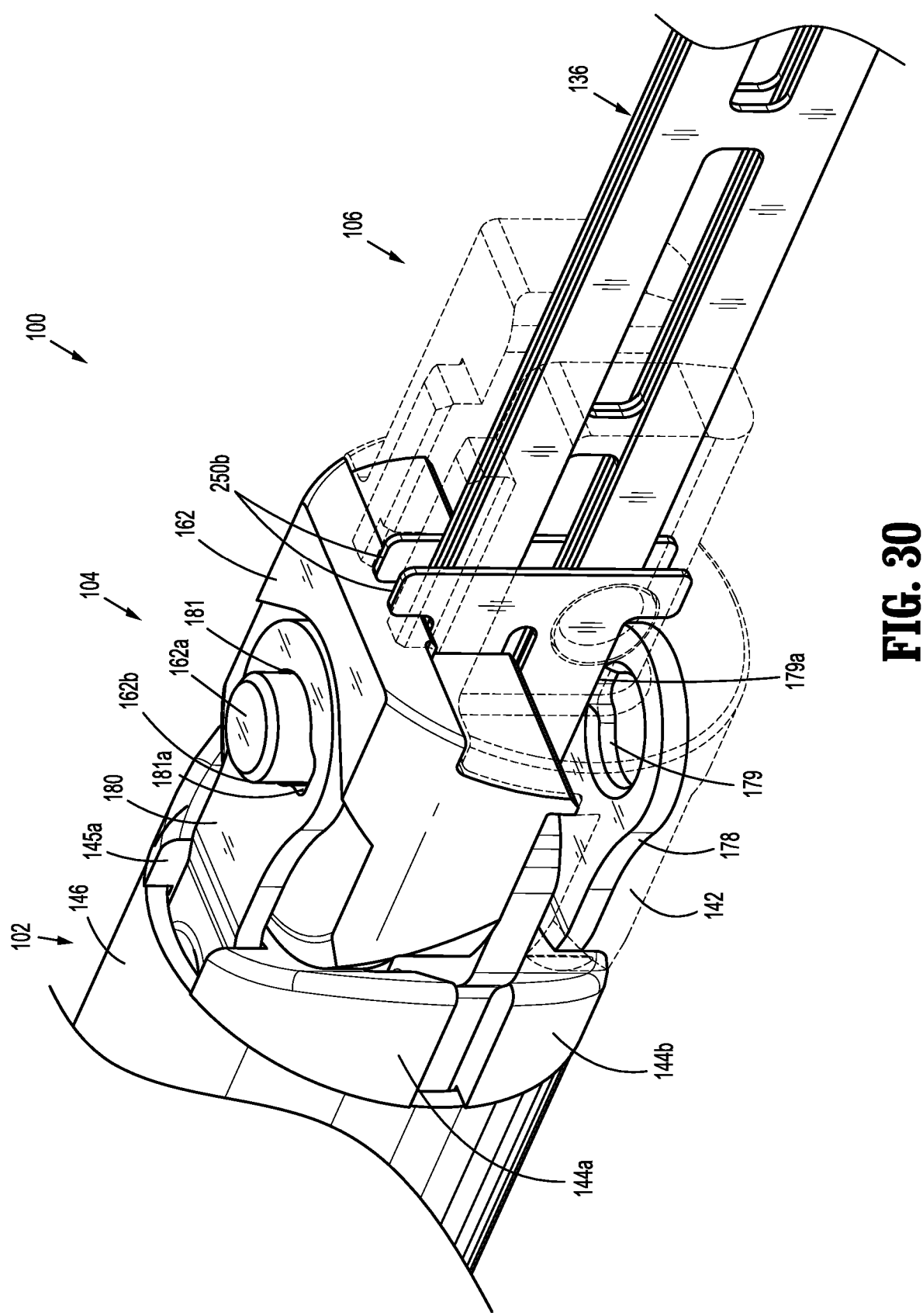
FIG. 30 is a perspective view of an articulating portion of the presently disclosed stapler reload including a mounting assembly.
Figure 31:
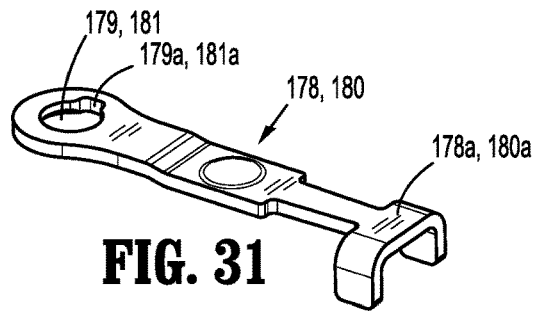
FIG. 31 is a perspective view of a coupling member according to an embodiment of the present disclosure.
Figure 32:
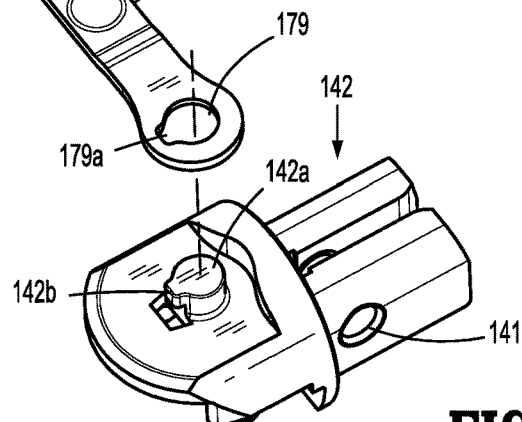
FIG. 32 is a perspective view of the coupling member shown in FIG. 31 and an upper mounting bracket of the mounting assembly shown in FIG. 30.

With reference briefly to FIGS. 24-26, as described above, the first articulation link 126 is releasably coupled to an articulation mechanism (not shown) of the adapter assembly 30 (FIG. 1) to control articulation of the tool assembly 106. More specifically, when the articulation mechanism of the adapter assembly 30 is operated, the first articulation link 126 is advanced (or retracted) to cause corresponding advancement (or retraction) of the second articulation link 138. The distal portion of the second articulation link 138 engages a first articulation member 140a which is pivotally connected to the pin member 182a of the lower mounting bracket 142 of the mounting assembly 104. As shown in FIG. 26, the pin member 182a is positioned at a location offset from the longitudinal axis of the body portion 102 such that longitudinal movement of the first articulation member 140a effects pivotal movement of the tool assembly 106 about a perpendicular axis, as indicated by arrow "F" in FIG. 24.

A second articulation member 140b is positioned parallel to the first articulation member 140a and engages the pin member 182b of the lower mounting bracket 142 of the mounting assembly 104. Each of the first and second articulation members 140a, 140b includes a curved support surface 141a, 141b, respectively, for supporting blow out plates 250 which extend between the body portion 102 and the tool assembly 106 of the stapler reload 100.

With reference to FIGS. 27-29, the stapler reload 100 includes a pneumatic seal 240 for creating a seal around the drive member 124 and the second articulation link 138. The pneumatic seal 240 includes a circular base portion 240a and a flange portion 240b extending from the base portion 240a. The base portion 240a is configured to fluidly seal a proximal portion of the inner body 144 of the small diameter portion 112 of the body portion 102 of the stapler reload 100. The flange portion 240b engages a proximal portion of the inner body 144 of the small diameter portion 112 of the body portion 102. The pneumatic seal 240 defines a central opening 241a for accommodating the drive member 124 in a sealing manner. The pneumatic seal 240 further defines a notch 241b for accommodating the second articulation link 138. The pneumatic seal 240 is disposed within the inner body 144 of the small diameter portion 112 of the body portion 102 and creates a seal between each of the drive member 124 and the second articulation link 138 and the inner body 144.

With reference now to FIGS. 30-34, the mounting assembly 104 of the stapler reload 100 includes the upper and lower mounting brackets 162, 142, and first and second coupling members 178, 180. As noted above, the first and second coupling members 178, 180 each include an opening 179, 181, respectively, for receiving pivot members 142a, 162a of respective lower and upper mounting brackets 142, 162. More particularly, each of the openings 179, 181 of the first and second coupling members 178, 180, respectively, include a notch 179a, 181a (FIG. 31) that receives the tab 142b, 162b (FIG. 30; shown in phantom) extending from the respective pivot members 142a, 162a of the upper and lower mounting brackets 162, 142. In this manner, each of the first and second coupling members 178, 180 is received about the respective pivot members 142a, 162a with the respective notches 179a, 181a of the respective first and second coupling members 178, 180 aligned with the respective tabs 142b, 162b of the respective pivot members 142a, 162a. The first and second coupling members 178, 180 are rotated from an unlocked position (FIG. 33), in which the first and second coupling members 178, 180 are disposed perpendicular to the longitudinal axis "x" of the stapler reload 100, to a locked position (FIG. 34) in which the first and second coupling members 178, 180 are disposed in alignment with the longitudinal axis "x" to secure the first and second coupling members 178, 180 to the respective lower and upper mounting brackets 142, 162. In this manner, the mounting assembly 104 creates a rivetless pivot assembly for articulating the tool assembly 106 of the stapler reload 100 relative to the body portion 102.

As described above, each of the upper and lower housing sections 120a, 120b of the body portion 102 include cutouts 145a, 145b (FIG. 5). Each of the first and second coupling members 178, 180 include folded portions 178a, 180a that are received within the cutouts 145a, 145b. The folded portions 178a, 180a of the respective first and second coupling members 178, 180 increase the strength of the engagement with the respective upper and lower half-sections 144a, 144b of the inner body 144 of the small diameter portion 112 of the body portion 102 of the stapler reload 100.

Figure 35:
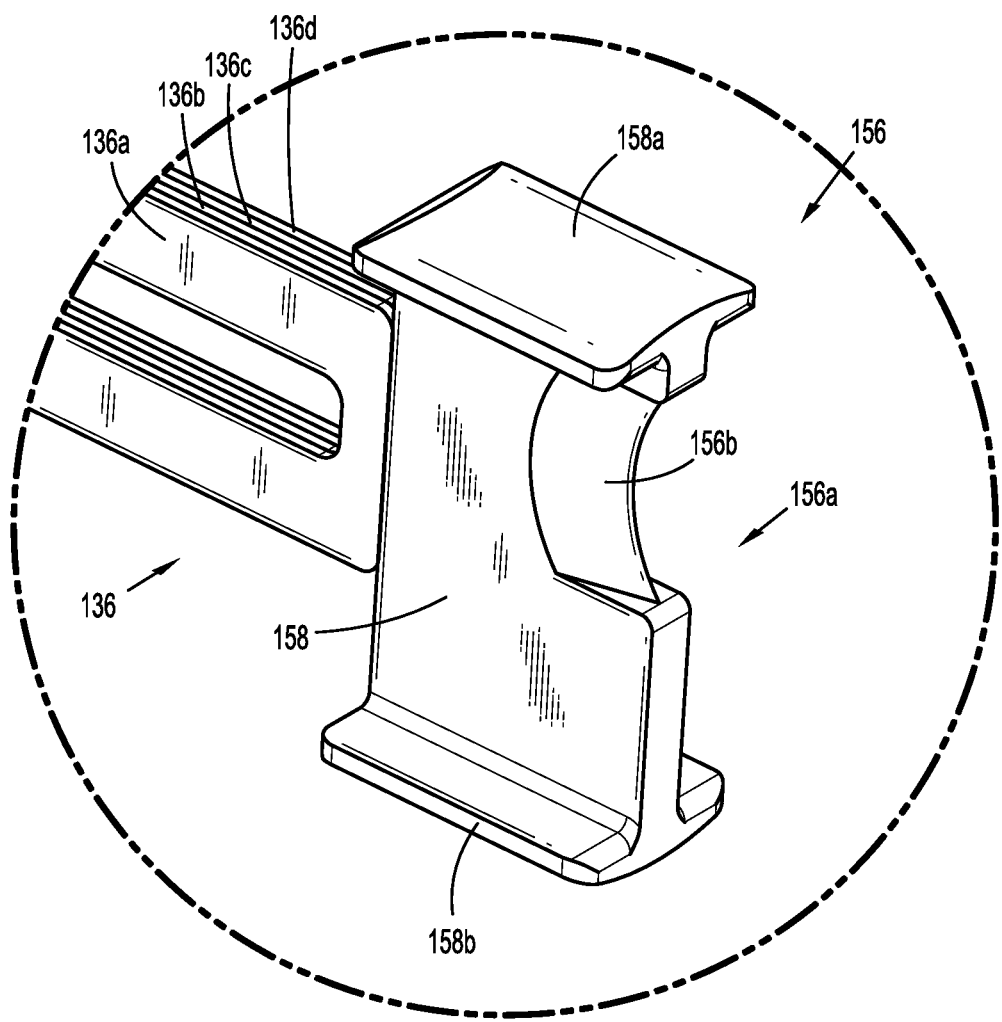
FIG. 35 is an enlarged section view of the indicated area of detail shown in FIG. 5.
Figure 36:
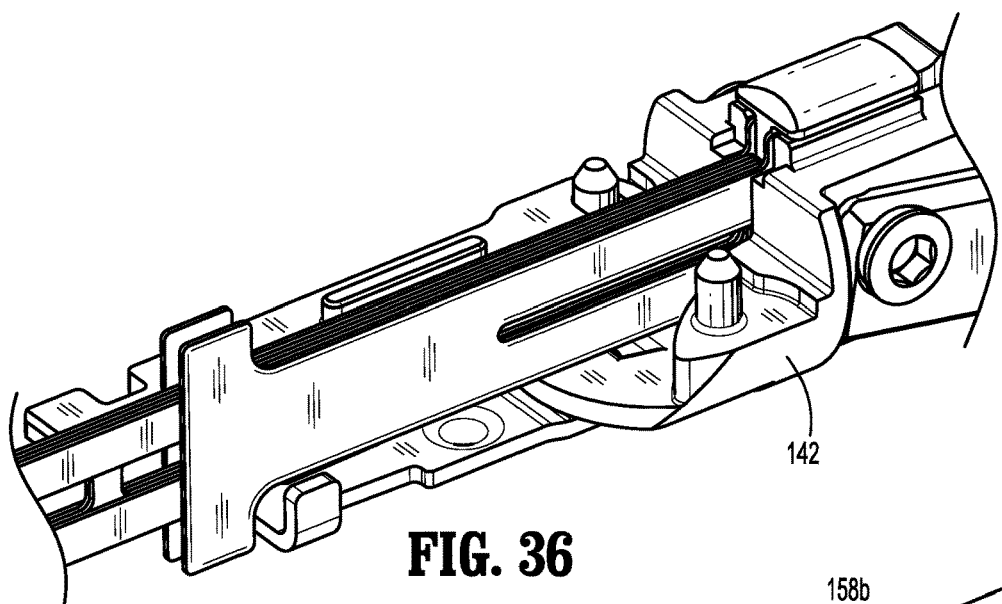
FIG. 36 is a perspective view of the articulating portion of the stapler reload shown in FIG. 30 with the upper mounting bracket of the mounting assembly and the cartridge assembly removed.

Referring to FIG. 35, in embodiments, the drive assembly 136 is formed from a plurality of stacked sheets 136a-d of a resilient material, e.g., stainless steel, spring steel. The distal portion of each of the sheets 136a-d of material of the drive assembly 136 is secured to the dynamic clamping member 156a such as by welding. The proximal ends of sheets 136a-d are hook-shaped and are received in the slot 125 in the distal portion of the drive member 124 such that longitudinal movement of the drive member 124 effects longitudinal movement of the drive assembly 136.

As best shown in FIG. 35, the dynamic clamping member 156a includes a knife 156b supported or formed on a vertical strut 158 of the dynamic clamping member 156a. The dynamic clamping member 156a includes an upper flange 158a and a lower flange 158b. The upper flange 158a is positioned to be slideably received within the cavity (not shown) of the anvil assembly 114 and the lower flange 158b is positioned to be slideably positioned along an outer surface 164a (FIG. 37) of the channel 164 of the cartridge assembly 116. In embodiments, either or both of the dynamic clamping member 156a and the channel 164 are lubricated with a hard coating. Distal movement of the drive assembly 136 initially advances the lower flange 158b into engagement with a cam surface 164b formed on the channel 164 to pivot the cartridge assembly 116 towards the anvil assembly 114 to a closed or approximated position (FIG. 38).

Thereafter, advancement of the drive assembly 136 progressively defines a maximum tissue gap between the anvil assembly 114 and cartridge assembly 116 adjacent the dynamic clamping member 156a as the dynamic clamping member 156a moves through the tool assembly 106. In embodiments, at least portions of the dynamic clamping member 156a and/or channel 164 are formed from and/or coated with a friction reducing material to minimize the force required to fire the surgical stapler 10 by facilitating substantially frictionless passage of the dynamic clamping member 156a through the stapler reload 100. For a detailed description of an exemplary drive assembly and dynamic clamping member, please refer to the '965 publication, the content of which was previously incorporated herein.

Figure 38:
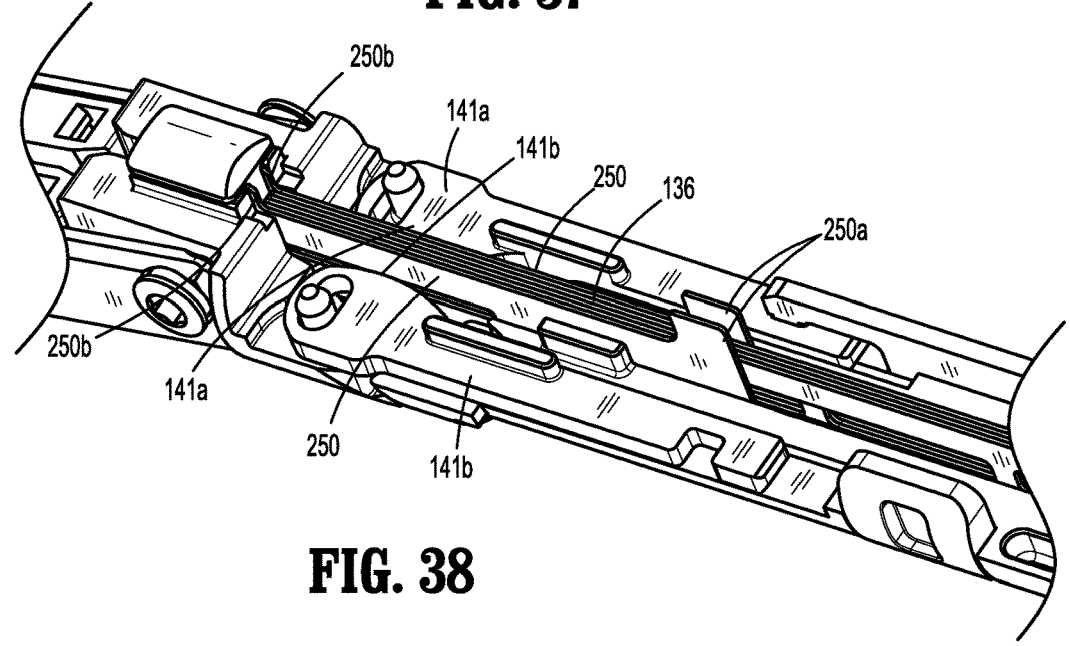
FIG. 38 is a perspective, top view of the distal portion of the small diameter portion of the stapler reload shown in FIGS. 1 and 2, with the upper mounting bracket and upper housing half-section removed.

With reference to FIG. 38, a blow-out plate 250 is positioned on each side of the drive assembly 136 to prevent buckling of the drive assembly 136 during straight and articulated firing of the stapler reload 100. The blow-out plates 250 extportion between the body portion 102 and the tool assembly 106 of the stapler reload 100. A distal portion 250b of each of the blow-out plates 250 is fixedly secured to the lower mounting bracket 142 of the mounting assembly 104. In embodiments, the distal portion 250a of each of the blow-out plates 250 is press fit within a slot (not shown) formed in the lower mounting bracket 142 (shown in phantom in FIG. 30) to axially fix the distal portion 250b of each of the blow-out plates 250 to the lower mounting bracket 142. Each of the first and second articulation members 140a, 140b includes curved portions 141a, 141b, respectively, for supporting an outer surface of the blow-out plates 250.

When the drive assembly 136 is advanced to advance the dynamic clamping member 156a through the cartridge body 170 to fire staples "S" with the tool assembly 106 in an articulated position, the blow-out plates 250 prevent the drive assembly 136 from buckling outward.

Figure 40:
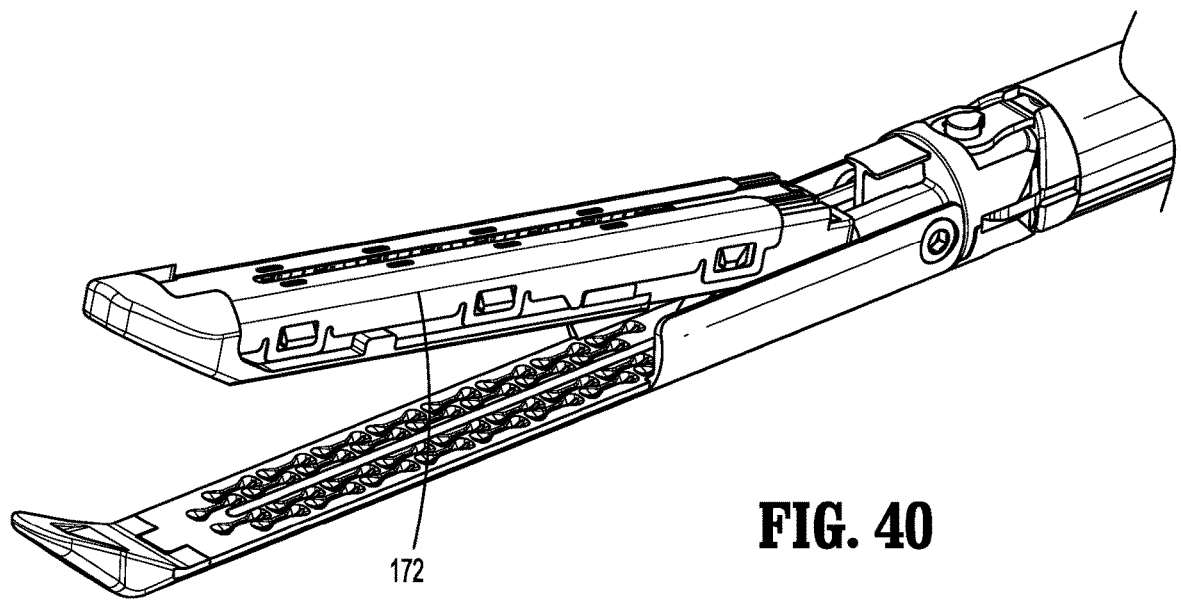
FIG. 40 is a perspective view of the tool assembly shown in FIG. 37, with the channel of the cartridge assembly removed.
Figure 41:
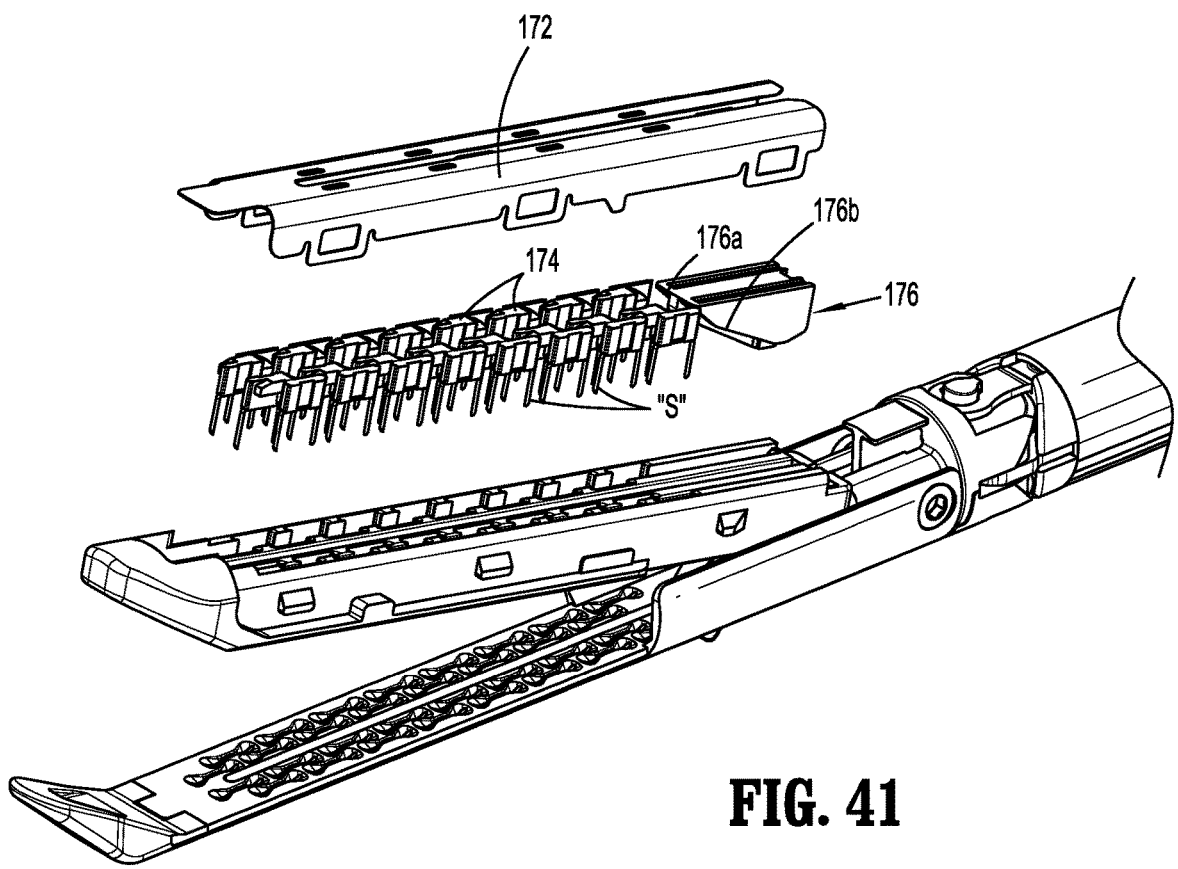
FIG. 41 is a perspective view of the cartridge assembly shown in FIG. 40, with parts separated.

Turning to FIGS. 40 and 41, the sled 176 is supported within the cartridge body 170 at a position immediately distal of the dynamic clamping member 156a. The distal portion of the dynamic clamping member 156a is positioned to engage and drive the sled 176 through the cartridge body 170 of the cartridge assembly 116. The sled 176 includes first and second cam members 176a, 176b that are positioned to engage the pushers 174 positioned within the cartridge assembly 116 to eject the staples "S" from the cartridge body 170. Each pusher 174 supports two staples "S" positioned on one side of the knife slot 171b of the cartridge body 170. As noted above, the cartridge assembly 116 includes the cartridge shield 172 for retaining the pushers 176 within the cartridge body 170. More particularly, the cartridge shield 172 allows the pushers 176 to be floating, and prevents the pushers 174 from exiting the staple retention slots 171a during transport.

Figure 42:
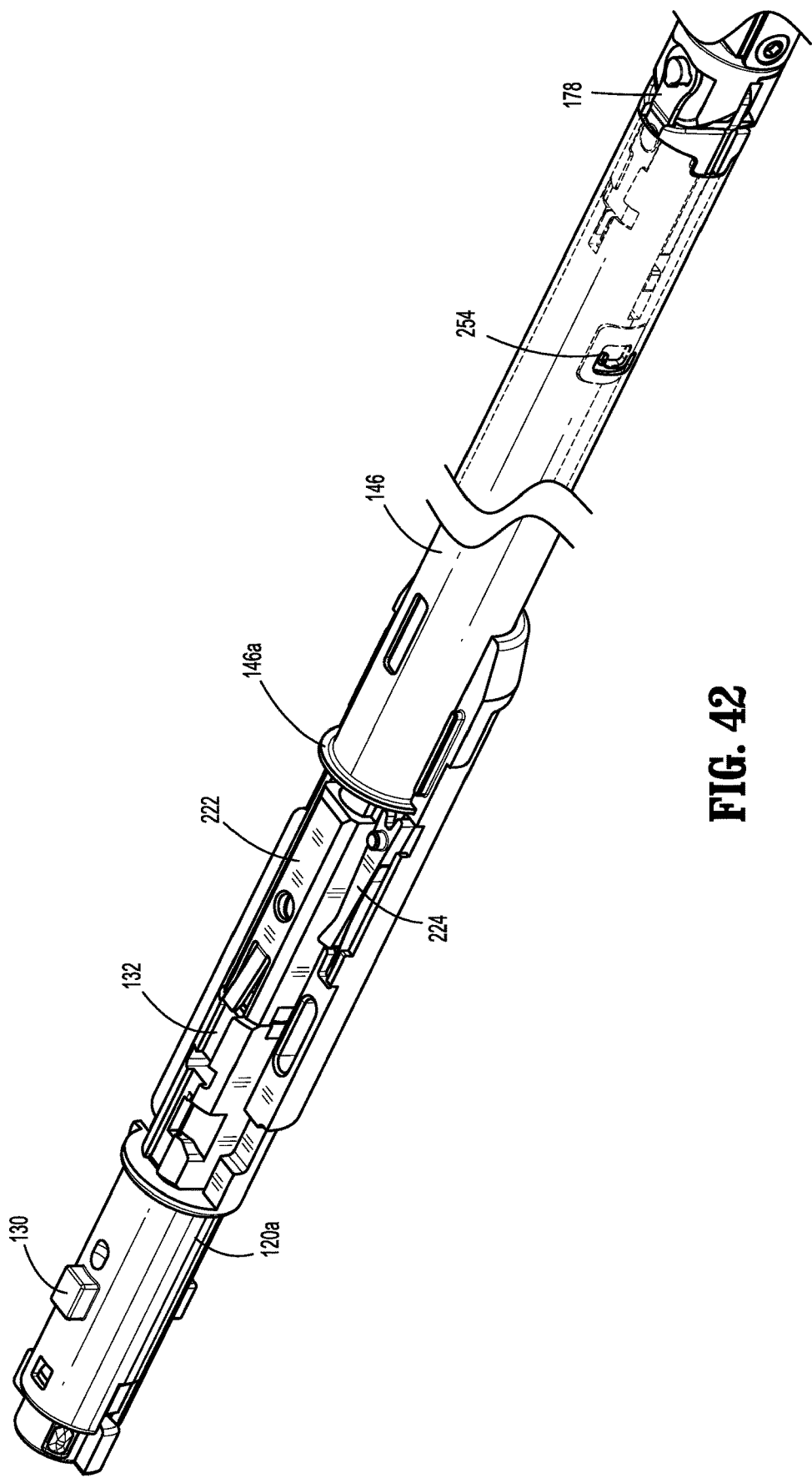
FIG. 42 is a perspective, top view of the body portion of the stapler reload shown in FIGS. 1 and 2, with the upper housing half-section and proximal tube body removed.
Figure 43:
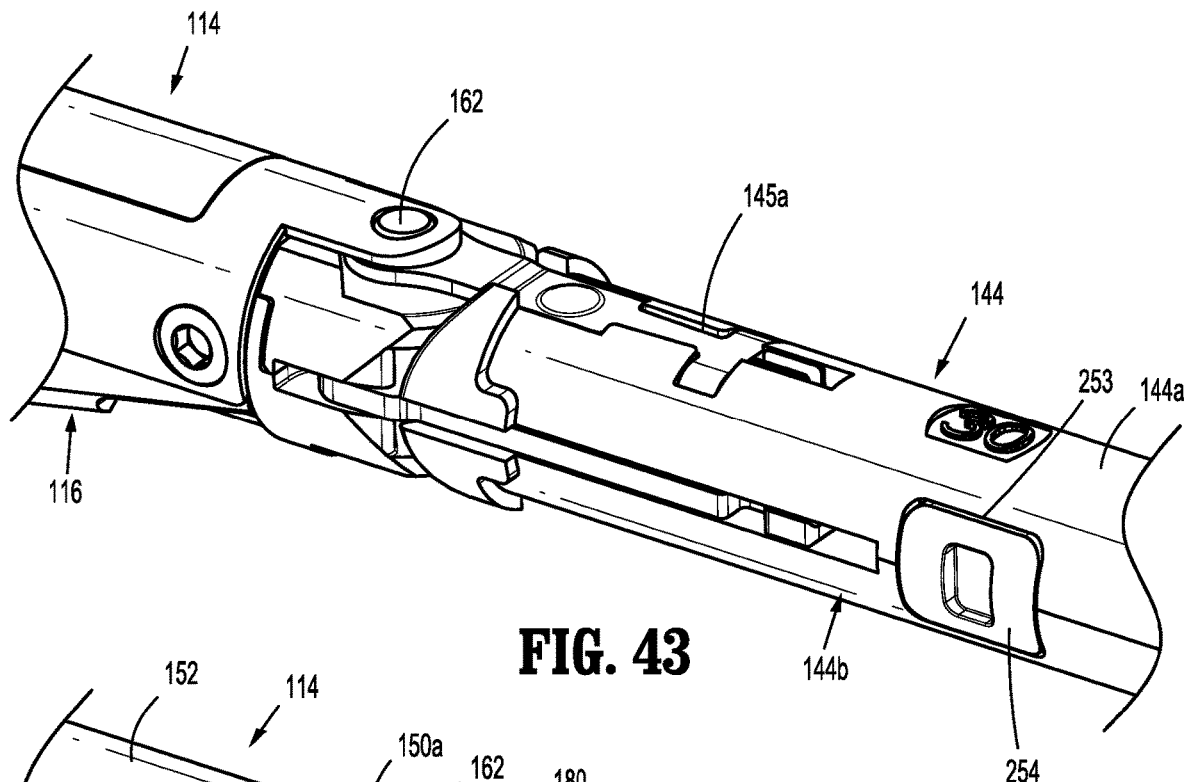
FIG. 43 is a perspective view of the articulating portion of the stapler reload shown in FIG. 30, with the outer tube of the small diameter portion removed.
Figure 44:
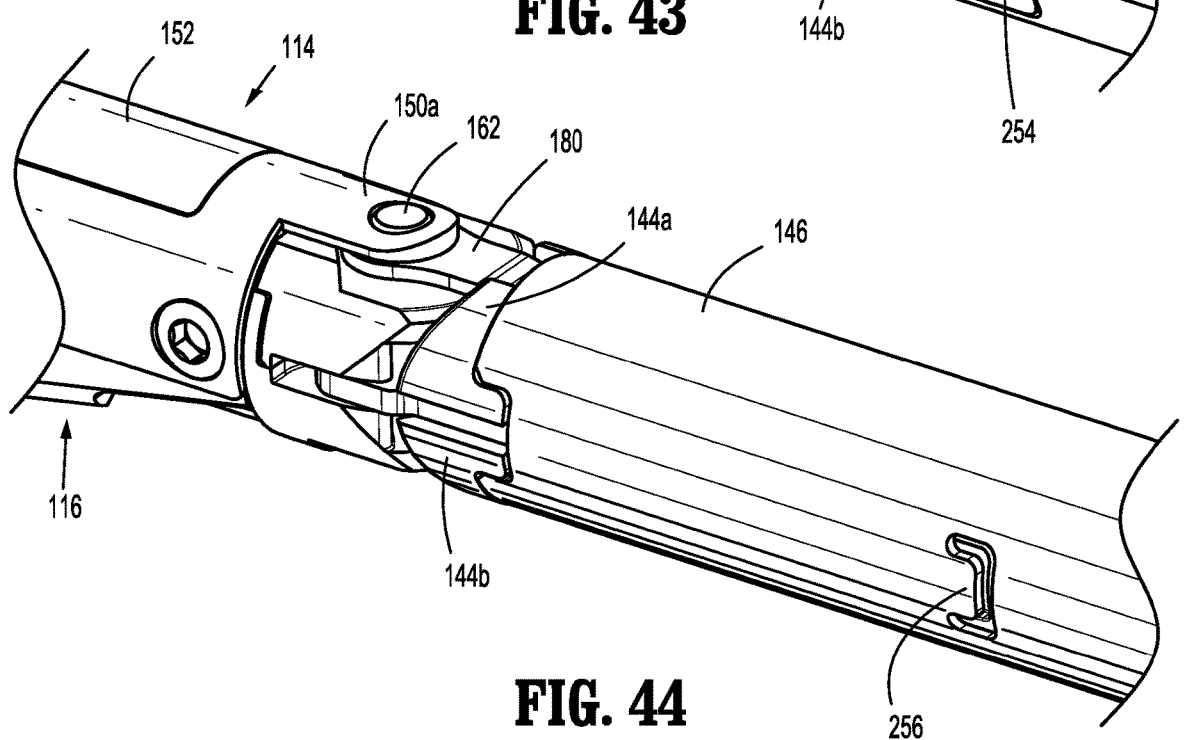
FIG. 44 is a perspective view of the assembled articulating portion of the stapler reload shown in FIG. 43.

With reference now to FIGS. 42-44, the surgical stapler 10 is configured to distribute actuation forces along a load path which enables the stapler reload 100 to have a smaller diameter. The load path begins with the knife 156b (FIG. 35) of the dynamic clamping member 156a (FIG. 35) of the drive assembly 136 (FIG. 35) cutting through tissue (not shown). More specifically, in the presently disclosed surgical stapler 10, the load is transferred from the dynamic clamping member 156a to the anvil and cartridge assemblies 114, 116 as the dynamic clamping member 156a travels therethrough. The load is then transferred from the anvil and cartridge assemblies 114, 116 to the lower mounting bracket 142 by pivot pins 168. The first and second pivot members 142a, 162a of the respective lower and upper mounting brackets 142, 162 of the mounting assembly 104 transfer the load from the lower and upper mounting brackets 142, 162 to the first and second coupling members 178, 180. The first and second coupling members 178, 180 transfer the load to the inner body 144 of the small diameter portion 112 of the body portion 102 of the stapler reload 100.

With particular reference now to FIG. 42, the inner body 104 of the small diameter portion 112 of the body portion 120 of the stapler reload 100 defines a cutout 253 for receiving a dinking plate 254. The dinking plate 254 is positioned to engage a dinking lance 256 located on the outer tube 146 of the small diameter portion 112 of the body portion 102 of the stapler reload 100. The dinking plate and lance 254, 256 operate to transfer the load from the inner body 104 of the small diameter portion 112 of the body portion 102 to the inner housing 120 of the large diameter portion 110 of the stapler reload 100. The inner housing 120 transfers the load to the actuation device 20 (FIG. 1) via the adapter assembly 30 (FIG. 1).

With reference now to FIGS. 45-50, another embodiment of a small diameter reload is shown generally as stapler reload 300. The stapler reload 300 is substantially similar to the stapler reload 100 described hereinabove except that the configuration of the shipping lock is changed, the location of the shipping lock is moved from the large diameter portion of the body portion to the small diameter portion of the body portion, and the configuration of the body portion and the tool assembly is modified to accommodate the changes in configuration and location of the shipping lock.

Referring initially to FIGS. 45 and 46, the stapler reload 300 includes a body portion 302, a mounting assembly 304, and a tool assembly 306. The body portion 302 defines a longitudinal axis "x" that is aligned with the longitudinal axis of the adapter assembly 30 (FIG. 1) and has a coupling portion 308, a large diameter portion 310, and an endoscopic or small diameter portion 312. The large diameter portion 310 of the stapler reload 300 has a diameter greater than the diameter of the small diameter portion 312. In embodiments, the small diameter portion 312 of the stapler reload 300 is dimensioned to be received in an 8 mm trocar assembly (not shown), whereas the large diameter portion 310 is about 12 mm in diameter. Alternately, other dimensions are envisioned.

The tool assembly 306 includes an anvil assembly 314 and a cartridge assembly 316. In embodiments, the cartridge assembly 316 is pivotally supported in relation to the anvil assembly 314 and is movable between an open position and a closed or approximated position. The mounting assembly 304 is supported on a distal portion of the small diameter portion 312 of the body portion 302 and pivotally supports the tool assembly 306 to facilitate articulation of the tool assembly 306 about an axis perpendicular to the longitudinal axis "x" of the body portion 302 between an articulated position in which a longitudinal axis of the tool assembly 306 defines an acute angle with the longitudinal axis "x" of the body portion 302 and a non-articulated position in which the longitudinal axes of the tool assembly 306 and the body portion 302 are aligned.

Figure 47:
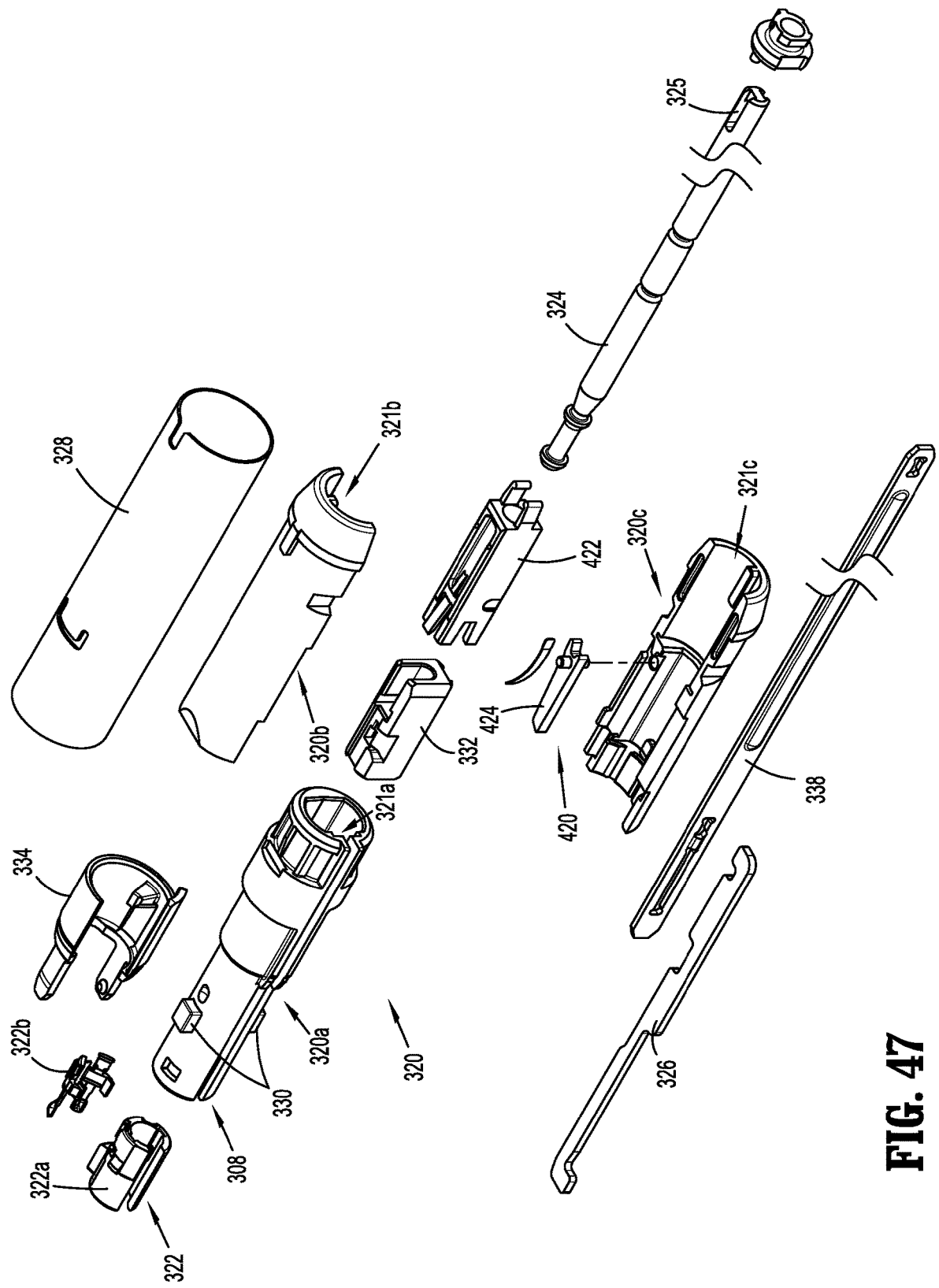
FIG. 47 is an exploded perspective view of a proximal portion of the stapler reload shown in FIG. 45.

With particular reference now to FIG. 47, the large diameter portion 310 of the body portion 302 of the stapler reload 300 includes an inner housing 320 having a proximal housing section 320*a*, an upper housing half-section 320*b*, and a lower housing half-section 320*c*. The upper and lower housing half-sections 320*b*, 320*c* are secured relative to each other with a tab and slot configuration about a distal end of the proximal housing section 320*a*. Alternately, the housing sections can be secured together in other suitable manners. The proximal housing section 320*a* and the upper and lower housing half-sections 320*b*, 320*c* define channels 321*a*, 321*b*, 321*c*, respectively, which slidably receive a drive member 324 and a first articulation link 326. The proximal housing section 320*a* and the upper and lower housing half-sections 320*b*, 320*c* are received within a proximal body tube 328 that prevents separation of the upper and lower housing half-sections 320*b*, 320*c* and, thus, prevents separation of the upper and lower housing half-sections 320*b*, 320*c* from the proximal housing section 320*a*.

The proximal portion of the upper housing half-section 320*a* defines the coupling portion 308 and includes engagement nubs 330 for releasably engaging the distal portion of the adapter assembly 30 (FIG. 1) in a bayonet-type coupling arrangement. For a detailed description of an exemplary coupling portion please refer to the '361 patent.

An electrical connector assembly 322 is supported within the proximal portion of the upper housing half-section 320*a* of the body portion 302 of the stapler reload 300. The connector assembly 322 includes a connector base 322*a* and a contact member 322*b* supported on the base 322*a*. For a detailed discussion of an exemplary electrical connection assembly, please refer to the '929 application.

The drive member 324 of the stapler reload 300 includes a proximal portion that supports a drive block 332. The drive block 332 releasably engages a control rod 32 (FIG. 2) of the adapter assembly 30 (FIG. 2) to translate movement of the control rod 32 into movement of the drive member 324. The drive block 332 is operably engaged by a rotatable sleeve 334 to prevent firing of the stapler reload 300 prior to the stapler reload 300 being properly secured to adapter assembly 20 (FIG. 1). The drive block 332 and the rotatable sleeve 334 of the stapler reload 300 are substantially similar in structure and operation to the drive block 132 and rotatable sleeve 134 of the stapler reload 100 described hereinabove. The first articulation link 326 and a second articulation link 338 are also substantially similar in structure and operation to the first and second articulation links 126, 138 of the stapler reload 100 described hereinabove.

The large diameter portion 310 of the body portion 302 of the stapler reload 300 further includes a lockout assembly 420 to prevent readvancement of the drive member 324 following firing of the stapler reload 300. The lockout assembly 420 includes a lockout shield 422 and a lockout member 424. The lockout assembly 420 operates in a similar manner to lockout assembly 220 of the stapler reload 100 described hereinabove.

By providing the stapler reload 300 with the large diameter portion 310 for housing the drive block 332 and the rotatable sleeve 334, as well as configuring the large diameter portion 310 to accommodate components of the stapler 10, the diameter of the small diameter portion 312 is minimized, for example, to about 8 mm such that it may be received within an 8 mm trocar assembly (not shown), while the large diameter portion 310 may be about 12 mm in diameter or larger.

Referring now to FIGS. 48 and 49, the small diameter portion 312 of the body portion 302 of the stapler reload 300 includes an inner body 344 received within an outer tube 346. The inner body 344 defines a channel 343 that slideably receives the drive member 324 (FIG. 47) and a drive assembly 336. A distal end of the drive assembly 336 includes a dynamic clamping member 356. The dynamic clamping member 356 includes a knife portion 356*a* and upper and lower flanges 358*a*, 358*b*. The upper flange 358*a* is positioned to be slideably received within a longitudinal cavity 313 of the anvil assembly 314 and the lower flange 358*b* is positioned to be slideably positioned along an outer surface 316*a* of the cartridge assembly 316. As described in detail above with regard to the stapler reload 100, initial distal movement of the drive assembly 336 causes pivoting of the cartridge assembly 316 towards the anvil assembly 314 to a closed or approximated position and continued distal movement of the drive assembly 336 within the tool assembly 306 effects the stapling and cutting of tissue (not shown).

Figure 50:
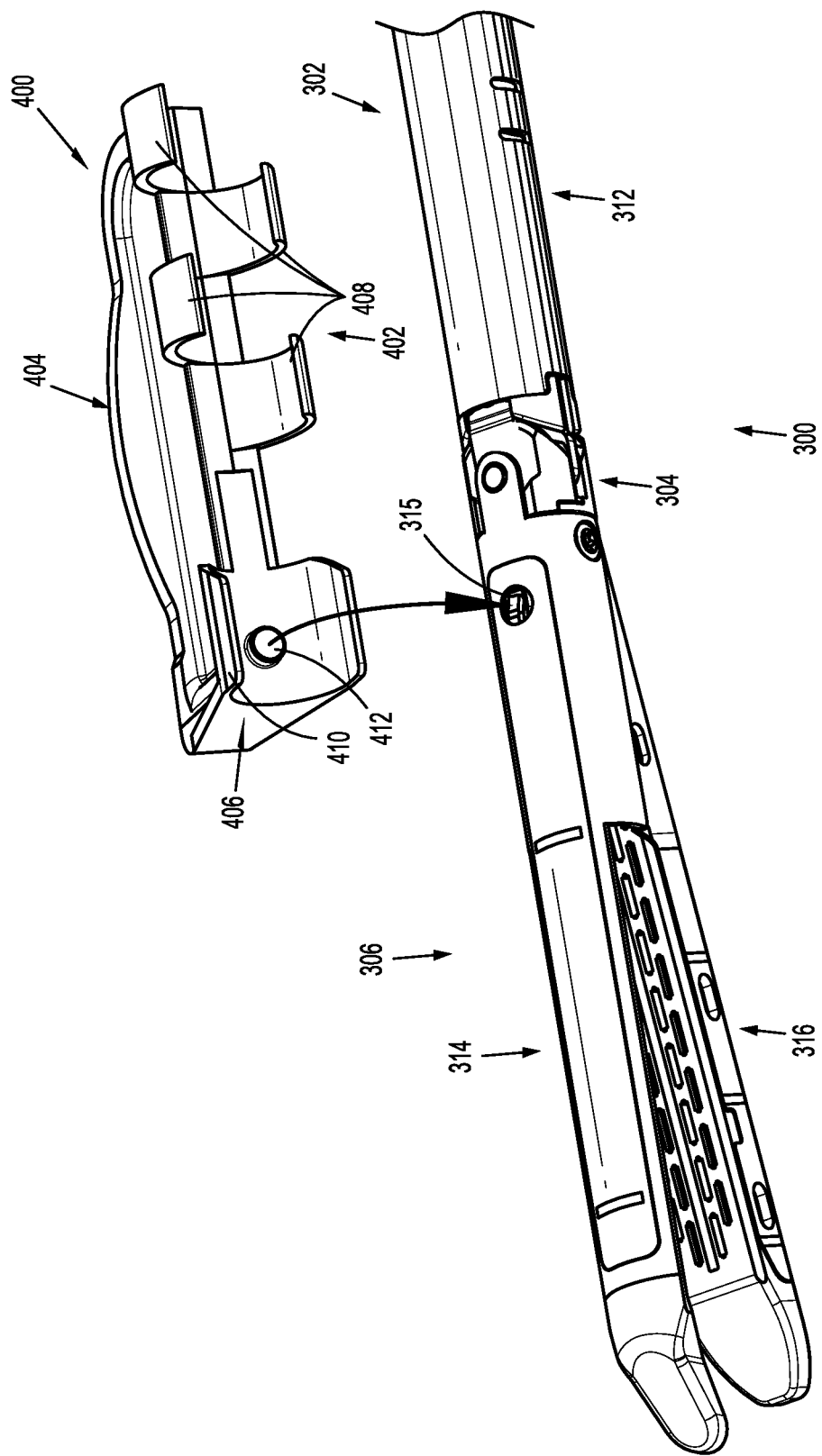
FIG. 50 is a side perspective view of the distal portion of the stapler reload and shipping lock shown in FIG. 46.

With additional reference to FIG. 50, the stapler reload 300 is provided with a shipping lock 400 configured to prevent operation of the stapler reload 300 when the shipping lock 400 is secured to the stapler reload 300. The shipping lock 400 is releasably secured to the small diameter portion 312 of the body portion 302 of the staple reload 300 and extends across the mounting assembly 304 and over a proximal portion of the tool assembly 306. The shipping lock 400 is configured to prevent advancement of the drive assembly 336 of the staple reload 300 and to prevent articulation of the tool assembly 306 relative to the body portion 302.

The shipping lock 400 includes an engagement portion 402, a handle portion 404, and a locking portion 406. The engagement portion 402 of the shipping lock 400 releasably secures the shipping lock 400 to the small diameter portion 312 of the body portion 302 of the stapler reload 300. More particularly, the engagement portion 402 includes a plurality of resilient, curved arms 408 that operate together to releasably grasp the small diameter portion 312 of the body portion 302. Although shown with two sets of opposed curved arms 408, it is envisioned that the shipping lock 400 may include any number of curved arms 408.

The handle portion 404 of the shipping lock 400 is configured to be grasped by a user and facilitate separation of the shipping lock 400 from the body portion 302 of the stapler reload 300. More particularly, the handle portion 404 of the shipping lock 400 permits the user to pull the shipping lock 400 radially outward from the body portion 302 of the stapler reload 300 to overcome the resilient force of the engagement portion 402 of the shipping lock 400 to release the shipping lock 400 from the body portion 302 of the stapler reload 300.

The locking portion 406 of the shipping lock 400 includes a locking flange 410 and a locking projection 412. The locking flange 410 is received about a proximal portion of the anvil assembly 314 of the tool assembly 306 to prevent articulation of the tool assembly 306 relative to the body portion 302. The locking projection 412 is configured to extend through an opening 315 in the proximal portion of the anvil assembly 314 into engagement with the dynamic clamping member 356 when the shipping lock 400 is secured to the stapler reload 300 to prevent advancement of the drive assembly 336. More particularly, the locking projection 412 of the shipping lock 400 engages the upper flange 358a of the dynamic clamping member 356 of the drive assembly 336 to prevent distal movement of the drive assembly 336.

Once the shipping lock 400 is separated from the stapler reload 300, the stapler reload 300 may be used in as described above with reference to the stapler reload 100.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapler comprising:
an actuation device;
a stapler reload releasably secured to the actuation device, the stapler reload including a body portion, a tool assembly, and a drive assembly movable within tool assembly, the body portion including a large diameter portion defining a first diameter and a small diameter portion defining a second diameter extending distally from the large diameter portion, the tool assembly being supported on a distal portion of the small diameter portion, wherein the small diameter portion is dimensioned to pass through an 8 mm trocar; and
a shipping lock releasably secured to the distal portion of the small diameter portion of the body portion and engagable with the drive assembly for preventing longitudinal movement of the drive assembly, wherein the shipping lock is releasable from the distal portion of the small diameter portion of the body portion prior to the stapler reload being secured to the actuation device.

2. The surgical stapler according to claim 1, wherein the shipping lock is configured to prevent articulation of the tool assembly relative to the body portion.

3. The surgical stapler according to claim 2, wherein the shipping lock includes a locking portion that engages the tool assembly to prevent articulation of the tool assembly relative to the body portion.

4. The surgical stapler according to claim 1, wherein the tool assembly includes an anvil assembly and a cartridge assembly supporting a plurality of staples and the drive assembly is movable through the tool assembly to eject the plurality of staples from the cartridge assembly.

5. The surgical stapler according to claim 1, wherein the drive assembly includes a clamping member and the shipping lock includes a projection, the projection engaging the clamping member when the shipping lock is secured to the body portion to obstruct advancement of the drive assembly.

6. The surgical stapler according to claim 5, wherein the clamping member includes an upper flange, the projection of the shipping lock engaging the upper flange to prevent advancement of the drive assembly.

7. The surgical stapler according to claim 1, wherein the shipping lock includes curved arms configured to frictionally engage the body portion of the stapler reload.

8. A surgical stapler comprising:
an actuation device;
a stapler reload releasably secured to the actuation device, the stapler reload including a body portion, a tool assembly, and a drive assembly movable within tool assembly, the body portion including a large diameter portion defining a first diameter and a small diameter portion defining a second diameter extending distally from the large diameter portion, the tool assembly being supported on a distal portion of the small diameter portion, wherein the small diameter portion is dimensioned to pass through an 8 mm trocar; and
a shipping lock releasably secured to the distal portion of the small diameter portion of the body portion and engagable with the drive assembly for preventing longitudinal movement of the drive assembly.

9. The surgical stapler according to claim 8, wherein the shipping lock is configured to prevent articulation of the tool assembly relative to the body portion.

10. The surgical stapler according to claim 9, wherein the shipping lock includes a locking portion that engages the tool assembly to prevent articulation of the tool assembly relative to the body portion.

11. The surgical stapler according to claim 8, wherein the tool assembly includes an anvil assembly and a cartridge assembly supporting a plurality of staples and the drive assembly is movable through the tool assembly to eject the plurality of staples from the cartridge assembly.

12. The surgical stapler according to claim 8, wherein the drive assembly includes a clamping member and the shipping lock includes a projection, the projection engaging the clamping member when the shipping lock is secured to the body portion to obstruct advancement of the drive assembly.

13. The surgical stapler according to claim 8, wherein the shipping lock includes curved arms configured to frictionally engage the body portion of the stapler reload.

* * * * *